(12) United States Patent
Nath et al.

(10) Patent No.: US 11,287,358 B1
(45) Date of Patent: **\*Mar. 29, 2022**

(54) MICROFLUIDIC ASPIRATOR AND MULTI-PURPOSE FLOW SENSOR AND METHODS OF MAKING AND USING THE SAME

(71) Applicant: Triad National Security, LLC, Los Alamos, NM (US)

(72) Inventors: Pulak Nath, Los Alamos, NM (US); Jackson Henry McFall, Los Alamos, NM (US); Dylan Chance Purcell, Los Alamos, NM (US); Jen-Huang Huang, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/538,561

(22) Filed: Aug. 12, 2019

Related U.S. Application Data

(63) Continuation-in-part of application No. 15/488,245, filed on Apr. 14, 2017, now Pat. No. 10,408,821.
(Continued)

(51) Int. Cl.
    *C12M 3/00* (2006.01)
    *B01L 3/00* (2006.01)
    (Continued)

(52) U.S. Cl.
    CPC ............ *G01N 11/08* (2013.01); *G01N 1/14* (2013.01); *G01N 33/5044* (2013.01)

(58) Field of Classification Search
    CPC ...... C12M 29/14; C12M 29/10; C12M 35/00; C12M 35/04
    See application file for complete search history.

(56) References Cited

U.S. PATENT DOCUMENTS

| 4,822,741 A | 4/1989 | Banes |
| 5,459,069 A | 10/1995 | Palsson et al. |
(Continued)

FOREIGN PATENT DOCUMENTS

WO    WO 2016/049363 A1    3/2016

OTHER PUBLICATIONS

Huang et al., "Non-pneumatic actuation of stretchable membranes with a novel microfluidic aspirator," *EMBS Micro and Nanotechnology in Medicine Conference*, Dec. 12-16, 2016 (1 page).
(Continued)

*Primary Examiner* — Nathan A Bowers
(74) *Attorney, Agent, or Firm* — Klarquist Sparkman, LLP

(57) ABSTRACT

Devices that include a liquid chamber including at least two ports, wherein the opening of a first port is larger than the opening of a second port, an air chamber including at least one port, and a membrane located between the liquid chamber and the air chamber, and a pressure sensor coupled to the port in the air chamber are provided. Systems including the disclosed devices are also provided. The systems include liquid in the liquid chamber of the device. Methods of using the devices and systems include measuring one or more properties of a liquid by flowing the liquid through the liquid chamber of the system and measuring the pressure produced due to the difference in size of the ports in the liquid chamber.

15 Claims, 25 Drawing Sheets

Related U.S. Application Data

(60) Provisional application No. 62/826,739, filed on Mar. 29, 2019, provisional application No. 62/322,577, filed on Apr. 14, 2016.

(51) Int. Cl.
*G01N 11/00* (2006.01)
*G01N 11/08* (2006.01)
*G01N 33/50* (2006.01)
*G01N 1/14* (2006.01)

(56) References Cited

U.S. PATENT DOCUMENTS

| 6,759,245 | B1* | 7/2004 | Toner | B01D 63/00 |
| | | | | 435/401 |
| 2004/0058408 | A1 | 3/2004 | Thomas et al. | |
| 2004/0132175 | A1 | 7/2004 | Vetillard et al. | |
| 2006/0270023 | A1 | 11/2006 | LeDuc et al. | |
| 2007/0116607 | A1* | 5/2007 | Wang | B01L 3/502715 |
| | | | | 422/83 |
| 2008/0280285 | A1* | 11/2008 | Chen | B01L 3/502715 |
| | | | | 435/5 |
| 2009/0088342 | A1 | 4/2009 | Moraes et al. | |
| 2011/0129911 | A1 | 6/2011 | Ahluwalia et al. | |
| 2014/0127798 | A1 | 5/2014 | Gordon et al. | |
| 2017/0299578 | A1* | 10/2017 | Nath | C12N 5/0688 |
| 2017/0335364 | A1 | 11/2017 | Viovy et al. | |
| 2018/0111128 | A1* | 4/2018 | Chatterjee | C12M 23/12 |

OTHER PUBLICATIONS

Iyer et al., "PulMo: A miniature, tissue-engineered lung," *2016 R&D 100 entry*, Apr. 15, 2016 (38 pages).

* cited by examiner

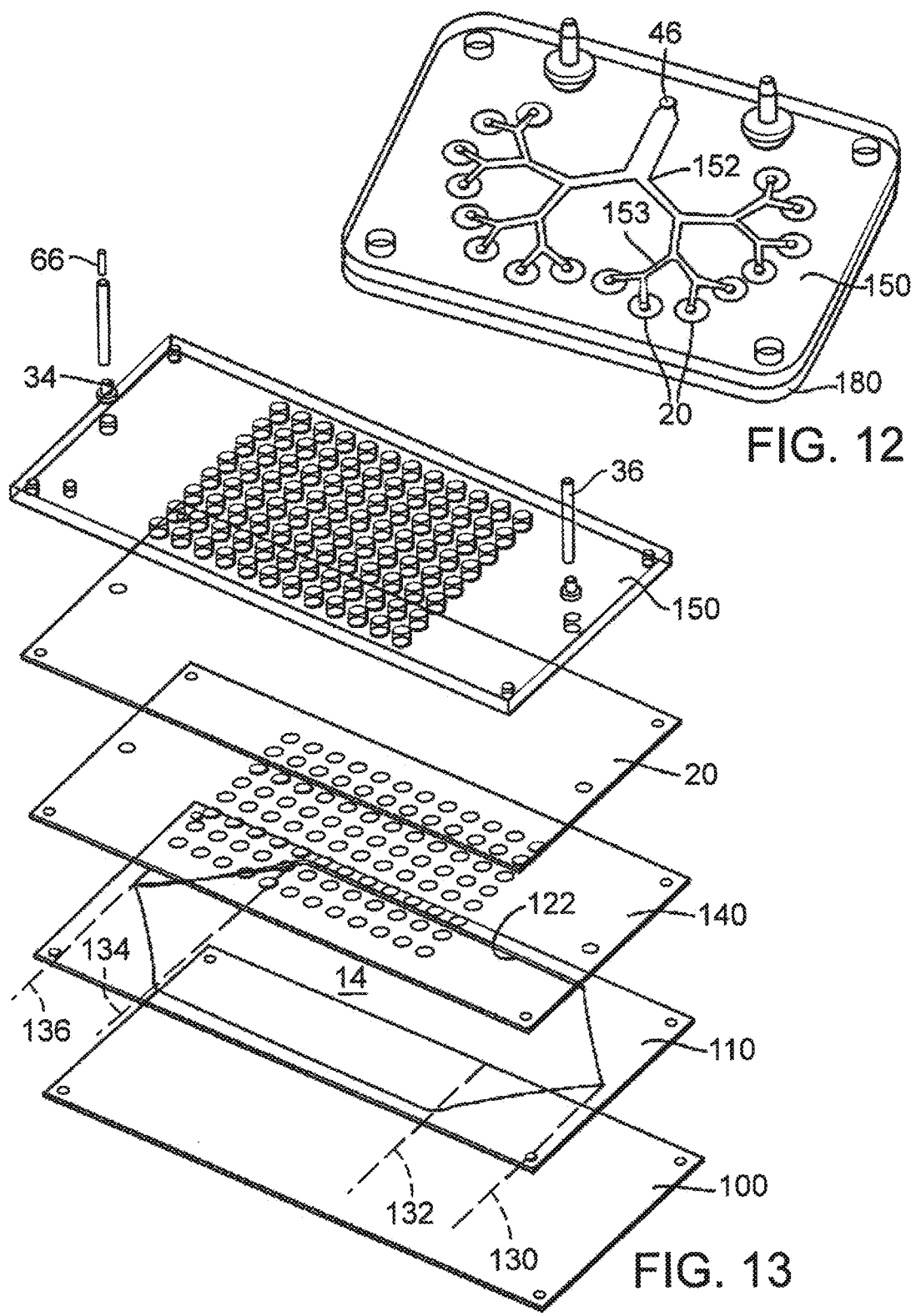

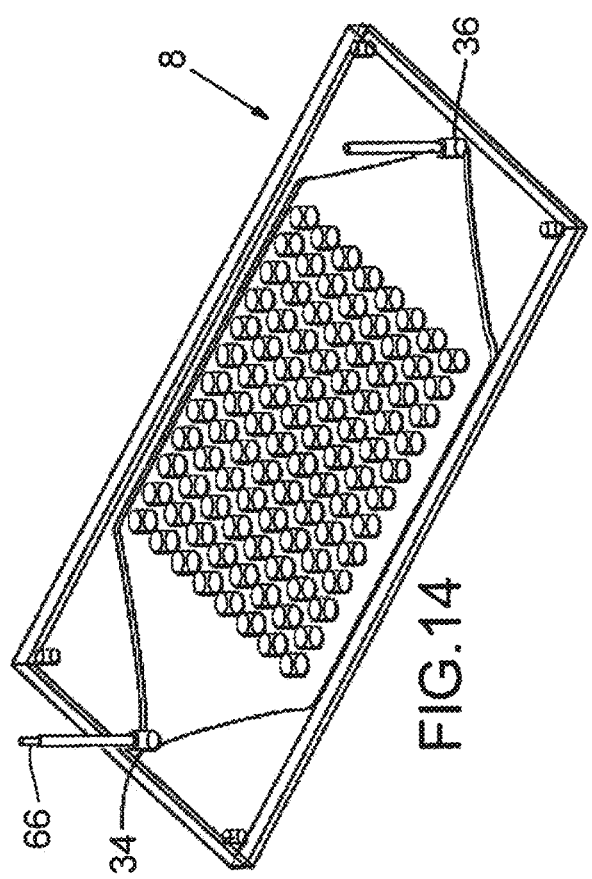
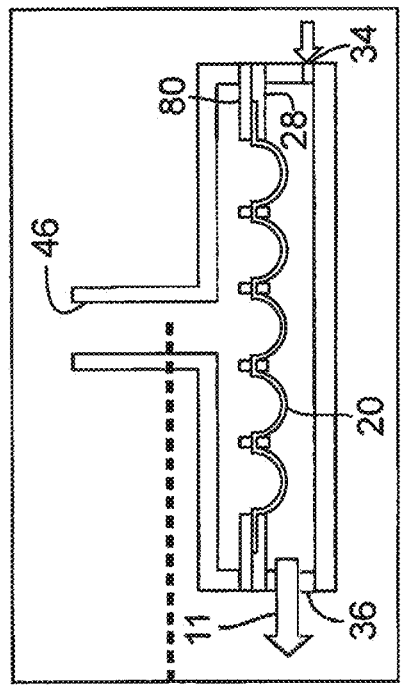
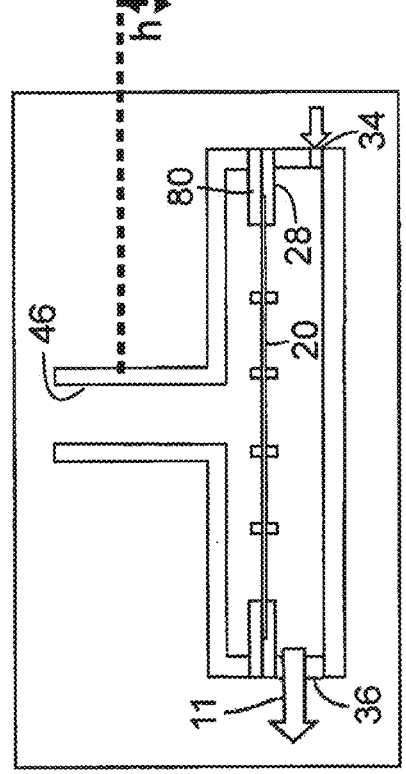

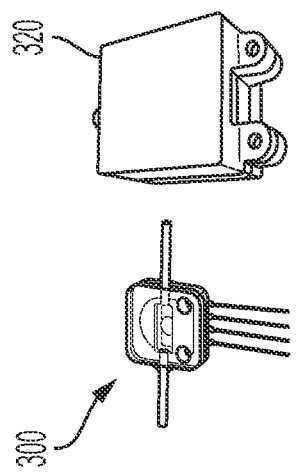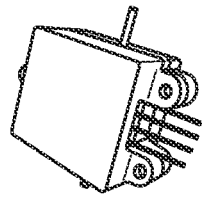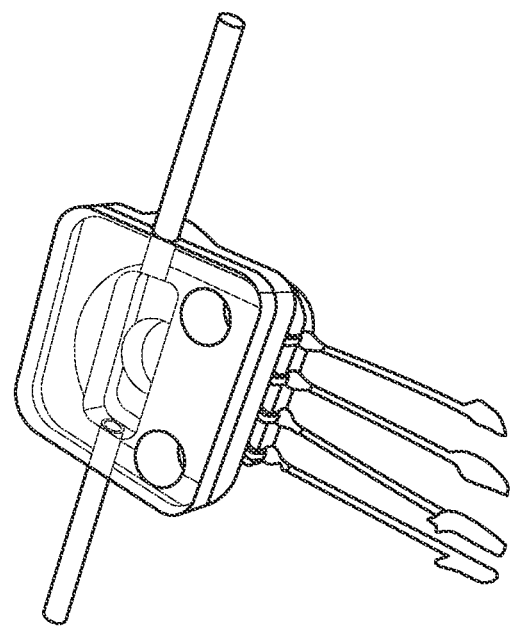
FIG. 25B
FIG. 25C
FIG. 25D

MICROFLUIDIC ASPIRATOR AND MULTI-PURPOSE FLOW SENSOR AND METHODS OF MAKING AND USING THE SAME

CROSS REFERENCE TO RELATED APPLICATION

This application is a continuation-in-part of co-pending U.S. application Ser. No. 15/488,245 filed Apr. 14, 2017, which in turn claims the benefit of U.S. Provisional Application No. 62/322,577 filed Apr. 14, 2016. This application also claims the benefit of U.S. Provisional Application No. 62/826,739, filed Mar. 29, 2019. All of which are incorporated herein by reference in their entireties.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

This disclosure relates to devices for creating a vacuum and methods of making and using the same, such as to mimic lung function, as well as devices and systems for measuring properties of a liquid and methods of making and using the same.

BACKGROUND

Lung diseases are some of the most common medical conditions in the world and are caused by factors such as smoking (including second-hand smoke), infections, and genetics. A key issue with pharmaceuticals is that approximately 90% of candidate drugs fail clinical trials due to lack of efficacy and/or toxicity. Even some pharmaceuticals that pass clinical trials are later found to have serious side effects. There are also thousands of compounds whose effects are currently unknown that could be potentially useful therapeutic compounds.

Further, measuring flow in microfluidic devices is typically carried out using flow sensors that are not integrated in the microfluidic systems. External units capable of measuring flow rates are typically used to achieve flow rates measurement, which adds peripherals and can limit miniaturization.

SUMMARY

In accordance with one aspect of certain embodiments, a need exists for devices that can more accurately determine physical and/or chemical properties of liquids, such as flow rate, viscosity, temperature, pH, and/or ion concentration. Disclosed herein are exemplary embodiments that can more accurately determine physical and/or chemical properties of a liquid, for example, over a larger dynamic range. Exemplary embodiments also provide advantages of small size (e.g., microfluidic scale), low cost, and convenience over currently available flow sensor devices.

In some embodiments, a device includes a housing including a liquid chamber including a first port and a second port, wherein the cross-sectional area of the second port is smaller than the cross-sectional area of the first port, an air chamber including a port; and a membrane between the liquid chamber and the air chamber, wherein the membrane has a boundary edge and first and second side surfaces, wherein at least a portion of the first side surface is fluidly coupled to the liquid chamber and at least a portion of the second side surface is fluidly coupled to the air chamber. The device also includes a pressure sensor coupled to the port in the air chamber and having at least one electrical connection that can provide an output.

In other embodiments, a device includes a housing including a liquid chamber including a first port and a second port, wherein the cross-sectional area of the first port and the second port are substantially the same; tubing connected to the second port, wherein at least a section of the tubing has a small cross-sectional area than the second port; an air chamber including a port; and a membrane between the liquid chamber and the air chamber, wherein the membrane has a boundary edge and first and second side surfaces, wherein at least a portion of the first side surface is fluidly coupled to the liquid chamber and at least a portion of the second side surface is fluidly coupled to the air chamber. The device also includes a pressure sensor coupled to the port in the air chamber and having at least one electrical connection that can provide an output.

In further embodiments, a device includes a housing including a liquid chamber including a first port and a second port, wherein the cross-sectional area of the first port and the second port are substantially the same; a packed bed within the second port, wherein the packed bed includes a stimulus-responsive material; an air chamber including a port; and a membrane between the liquid chamber and the air chamber, wherein the membrane has a boundary edge and first and second side surfaces, wherein at least a portion of the first side surface is fluidly coupled to the liquid chamber and at least a portion of the second side surface is fluidly coupled to the air chamber. The device also includes a pressure sensor coupled to the port in the air chamber and having at least one electrical connection that can provide an output. In some examples, the stimulus-responsive material is responsive to temperature, pH, and/or ion concentration, such as a pH responsive hydrogel, an ion-exchange resin, or a thermo-responsive gel.

Also disclosed are systems including the disclosed devices. The systems include a disclosed device a liquid reservoir coupled to the second port, and a pump fluidly coupled to the first port. In some embodiments, the system further includes an electronic module (such as a computer) coupled to an electrical connection of the pressure sensor. The system can also include liquid in the liquid chamber.

Methods of using the devices and systems are also disclosed. In some examples, the methods include determining liquid flow rate, including pumping liquid into the first port of the liquid chamber or pumping liquid out of the first port of the liquid chamber of the system; measuring the pressure in the air chamber produced by pumping the liquid; and determining the liquid flow rate (for example, using a reference value or table or standard curve). In other examples, the methods include determining liquid viscosity, including pumping liquid into the first port of the liquid chamber or pumping liquid out of the first port of the liquid chamber of the system; measuring the pressure in the air chamber produced by pumping the liquid; and determining the viscosity of the liquid (for example, using a reference value or table or standard curve). In additional examples, the methods include determining a characteristic of a liquid (such as temperature, pH, or ion concentration), including pumping liquid into the first port of the liquid chamber or pumping liquid out of the first port of a device including a stimulus-responsive material; measuring the pressure in the air chamber produced by pumping the liquid; and determining the characteristic of the liquid, wherein the characteristic of the liquid is one that causes the stimulus-responsive packed bed in the second port to swell or expand. The characteristic of the liquid may be determined using a reference value or table or standard curve The foregoing and other features of the disclosure will become more apparent from the following detailed description, which proceeds with reference to the accompanying figures.

BRIEF DESCRIPTION OF THE DRAWINGS

FIG. 12 is a schematic illustration of an alternative embodiment of an exemplary lung device including an embodiment of an aspirator as disclosed herein.

FIG. 13 is an exploded view of an exemplary ninety-six well embodiment of an aspirator in accordance with this disclosure.

FIG. 14 is a perspective view of the assembled aspirator of FIG. 13.

FIG. 15 is a schematic illustration showing use of an exemplary embodiment for measuring flow rate and/or viscosity of a fluid.

FIG. 24A illustrates a state of positive pressure in the liquid chamber generated by infusing liquid into a first port, resulting in deflection of the membrane into the air chamber. FIG. 24B illustrates a state of negative pressure in the liquid chamber generated by withdrawing liquid from the first port, resulting in deflection of the membrane into the liquid chamber. Arrows indicate the direction of fluid flow.

FIGS. 25A-25D are images showing an embodiment of the flow sensor. FIGS. 25A and 25B illustrate the flow sensor. Scale bar=1 mm. FIG. 25C shows the flow sensor (left) and a casing for the sensor (right) and FIG. 25D shows the flow sensor placed in the casing.

FIG. 26A shows pressure at a given flow rate for infused liquid flow through the first port. FIG. 26B shows pressure at a given flow rate for withdrawal liquid flow through the first port.

DETAILED DESCRIPTION

I. Explanation of Terms

Figure 1:
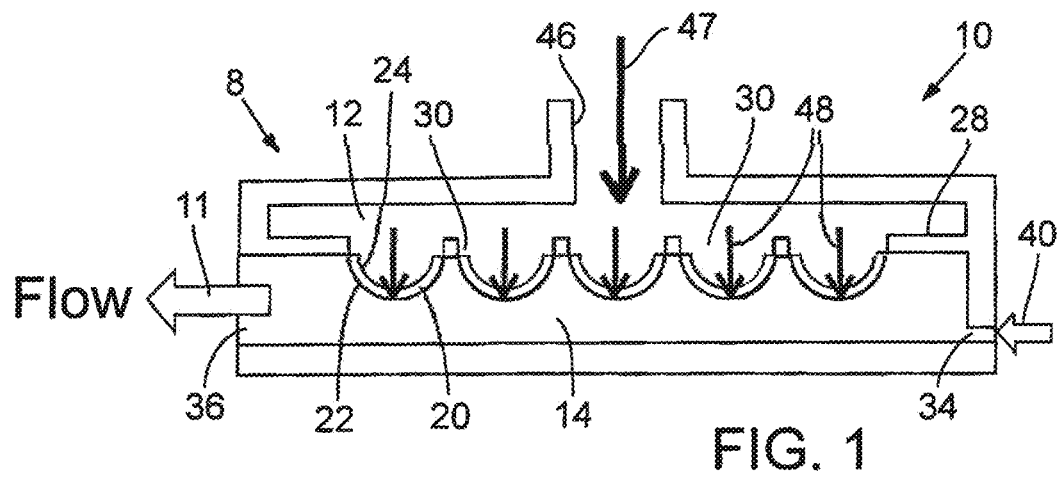
FIGS. 1 and 2 are schematic illustrations showing cross-sectional views of an exemplary embodiment of a disclosed aspirator device in a flow ("inhale") configuration (FIG. 1) and a stop flow ("exhale") configuration (FIG. 2).

The following explanations of terms are provided to better describe the present disclosure and to guide those of ordinary skill in the art in the practice of the present disclosure. As used herein, the words "including" and "having" and their formatives have the same meaning as "comprising and its corresponding formatives. Also, the singular forms "a" or "an" or "the" include plural references unless the context clearly dictates otherwise. The term "or" refers to a single element of stated alternative elements or a combination of two or more elements, unless the context clearly indicates otherwise. The term "coupled to" (e.g. element A is coupled to element B) includes direct connection of the elements and also includes indirect connection of the elements through one or more other elements.

Any theories of operation are to facilitate explanation, but the disclosed devices, materials, and methods are not limited to such theories of operation. Although the operations of some of the disclosed methods are described in a particular, sequential order for convenient presentation, it will be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed components and materials can be used in conjunction with other components and materials. Additionally, the description sometimes uses terms such as "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or devices are referred to as "lowest," "best," "minimum," or the like. It will be appreciated that such descriptions are intended to indicate that a selection among many used functional alternatives can be made, and such selections need not be better, smaller, or otherwise preferable to other selections.

Examples are described with reference to directions indicated as "above," "below," "upper," "lower," "top", "bottom" and the like. These terms are used for convenient description, but do not imply or require any particular spatial orientation. For example, if an apparatus has two chambers and can be oriented with a first chamber above the second chamber, the first chamber that is above the second chamber can be called a top chamber. If the orientation is changed such that the chambers are vertical or reversed with the second chamber above the first chamber, the apparatus still has a top chamber (the first chamber is still a top chamber, even though it is now oriented on the bottom). The term "and/or" is to be broadly construed to include all possible combinations of elements or items with which the term is used, as well as the elements or items individually.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims. Furthermore, not all alternatives recited herein are equivalents.

II. Device Embodiments

Disclosed herein are devices that can be utilized to create a vacuum, for example, in a microfluidic environment. As discussed below, the devices can be used to simulate breathing without using air pumps to introduce air into the device, and by producing mechanical stretch of the membrane (and any associated cells) without using pneumatic sources. In addition to providing a more physiological model, the disclosed devices reduce instrumentation complexity, simplify operation, and reduce cost compared to current lung models.

In the disclosed devices, the membrane component is actuated to produce mechanical stretch of the membrane and create a reduction in pressure or a vacuum in the top chamber. Briefly, liquid is flowed through the bottom chamber of the device. A restriction is provided in the flow path such as at an inlet or upstream from the inlet to the bottom chamber. The restriction has a smaller cross sectional area than the liquid outlet, and a smaller cross sectional area than the total cross sectional area of all of the outlets if more than one outlet. For example, the restriction can be positioned upstream from the aspirator in a liquid flow path or incorporated into the one or more inlets, such as by providing inlets with a total cross sectional area that is less that the cross sectional area of the outlets. The inlet can, for example, be internal to the aspirator or at the entrance to the aspirator bottom chamber. When the liquid is pumped from the outlet, a pressure drop is created in the bottom chamber, creating a pressure drop or vacuum in the top chamber resulting from an expansion of the membrane into the lower chamber ("into" includes "toward"). As a result, the membrane(s) stretch into the bottom chamber. If there is an open port in the top chamber, the vacuum produces air or gas intake or inhaling (or fluid movement into the top chamber). When flow in the bottom chamber is stopped, or the flow rate is reduced, the pressure drops in the bottom chamber. For example, if the flow is stopped, pressure in the bottom chamber equilibrates causing the membrane(s) to relax back to their starting position (or to substantially their starting position). If there is an open port in the top chamber, the pressure equilibration produces air or gas outflow or exhaling (or fluid movement out of the top chamber, if the top chamber contains fluid). The pressure drop in the lower chamber can be controlled by controlling the pumping rate of liquid out of the lower chamber, although stopping and starting the pump is a desirable option to control inhaling into and exhaling from the top chamber. The pressure in the bottom chamber can alternatively be caused to rise more rapidly in the bottom chamber by reversing the pump to pump liquid through the outlet and into the lower chamber.

FIG. 1 depicts an embodiment 8 of an apparatus in a first operating (liquid is flowing through the bottom chamber in the direction indicated by arrow 11 configuration. The FIG. 1 apparatus includes a housing 10 having a top chamber 12, a bottom chamber 14 and a membrane 20. The membrane comprises an edge boundary and opposed first and second major side surfaces. In FIG. 1, the first side surface 22 faces toward bottom chamber 14 and the second side surface 24 faces the top chamber 12. The membrane 20 is positioned in this embodiment between top chamber 12 and bottom chamber 14. The side 24 of membrane 20 is fluidly coupled with top chamber 12 and the side 22 of membrane 20 is fluidly coupled with bottom chamber 14. In some examples, the apparatus desirably also includes a first substrate 28 between top chamber 12 and bottom chamber 14. Substrate 28 includes one or more openings, some of which are indicated at 30 in FIG. 1. The membrane 20 spans these openings. Although not shown in the schematic view of FIG. 1, typically the membrane is continuous across all of the openings. In some embodiments, as discussed below, membrane 20 is sandwiched between two substrate layers. The example depicted in FIG. 1 is an embodiment with five openings or wells 30 in substrate 28.

The device also includes at least one liquid inlet 34 and at least one liquid outlet 36. The outlet 36 is desirably located at a different side or end of the bottom chamber 14 from the inlet 34, for example, in a wall of the bottom chamber opposite to inlet 34. Although the embodiments illustrated herein show inlet 34 and outlet 36 as being substantially aligned and on opposite ends of the bottom chamber, additional configurations can be utilized, including having the inlet and outlet on opposite sides of the bottom chamber, but not aligned with one another or having the inlet and outlet on adjacent sides of the bottom chamber and/or extending upwardly through the top of the bottom chamber from opposite ends of the bottom chamber. In the example of FIG. 1, inlet 34 is smaller (for example in diameter or cross-sectional area) than outlet 36 and thus is one example of a constriction in the liquid flow path. Arrow 40 illustrates the flow of liquid into the lower chamber 14 through the inlet 34. The inlet and outlet may have any cross-sectional shape, including circular, rectangular, square, oval, or other shapes.

Top chamber 1 in FIG. 1 also can include a port 46, which in some embodiments is an air or gas inlet/outlet port. The port 46 in FIG. 1 communicates with top chamber 12. In FIG. 1, the port 46 is depicted on the upper (top) surface of the top chamber, but the port can be located at any position on the top or side surfaces of the top chamber or otherwise to communicate with the top chamber. In some embodiments, top chamber 12 contains air or gas and bottom chamber 14 contains a liquid. As discussed below, during the flow of a liquid through bottom chamber 14 from inlet 34 to outlet 36, arising from pumping liquid from outlet 36, a pressure drop is created in the bottom chamber, resulting in a vacuum or pressure reduction in top chamber 12. In response to the pressure drop in the bottom chamber, the membrane 20 expands into the openings 30 toward the bottom chamber and can, in some embodiments expand into the bottom chamber. This draws or inhales air or gas (as indicated by arrow 47) into the port 46. The deforming of membrane 20 toward, and in this example into, the bottom chamber 14 through the openings 30 in response to the pressure drop is illustrated by the arrows 48.

Figure 2:
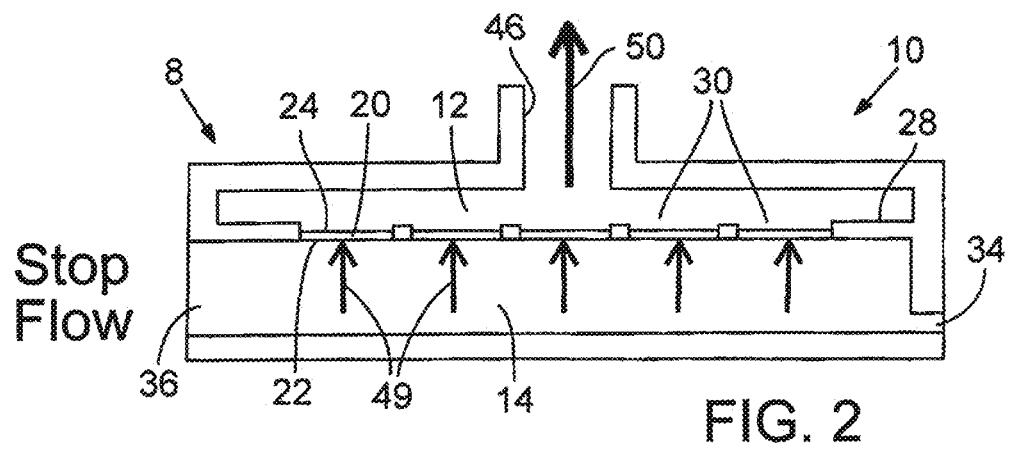

FIG. 2 depicts the FIG. 1 embodiment in a resting (stop flow) position. When there is no flow or a reduced flow through bottom chamber 14, the pressure in the chamber is in equilibrium with the pressure in the upper chamber, if for example the upper chamber is at ambient pressure. Under these conditions, the membrane 20 moves toward the top chamber, as indicated by arrows 49, and the membrane achieves a relaxed position as shown in FIG. 2. In response to this relaxation of membrane 20, and assuming the upper port 46 is coupled to the atmosphere, gas is pushed out of the upper chamber 12 (exhales) as indicated by arrow 50. The pressure in the bottom chamber can be repeatedly decreased and increased to create inhaling and exhaling breathing cycles to mimic lung function. Although specific embodiments of the devices are illustrated herein, the number positioning, size, and shape of inlet(s), outlet(s), port(s), and openings in the device and the size and shape of the chambers are only exemplary. Additional configurations can also be utilized and are within the scope of this disclosure.

Figure 3:
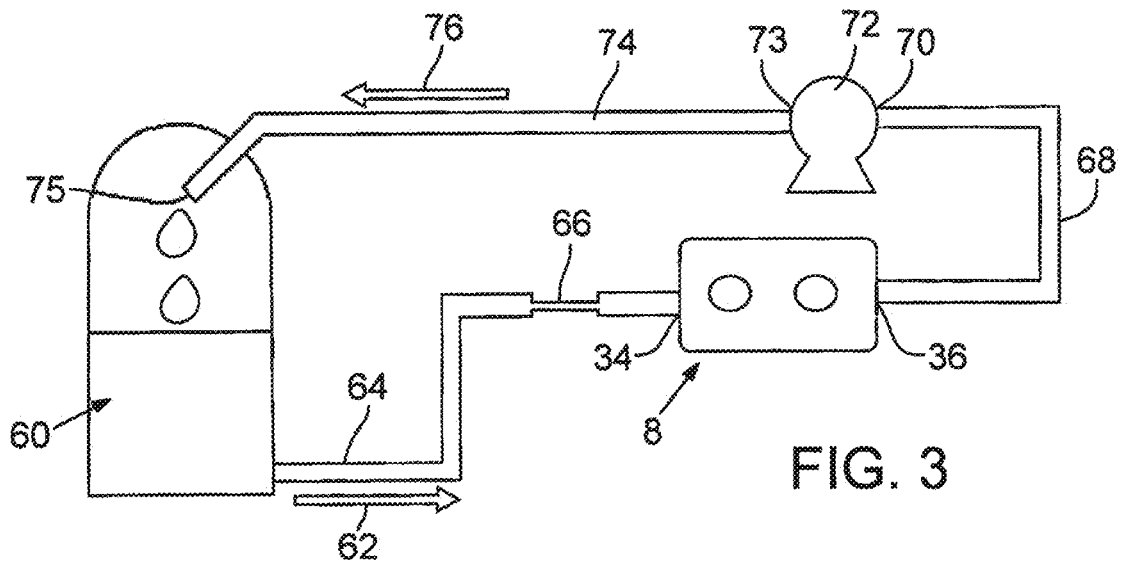
FIG. 3 is a schematic illustration of a pump system including a source of liquid and a flow path through an exemplary embodiment of an aspirator.

FIG. 3 illustrates and exemplary system including an aspirator in accordance with this disclosure, such as the aspirator 8. In FIG. 3, a source of liquid 60 is shown, such as a supply tank which can be maintained in sterile conditions and that can be included in a closed loop system. A fluid flow path is provided from upstream source 10 in a downstream direction indicated by arrow 62. The fluid flow path in this example includes a first tubing section 64 from source 60 to aspirator inlet 34. In this example, the flow restriction is included in tubing section 64 and is shown at 66 at a location upstream from the inlet 34. In this case, the inlet 34 may or may not include a further restriction to liquid flow. The liquid enters inlet 34 and flows through the bottom chamber or chambers of the aspirator 8 to the outlet 36. From outlet 36, the flow path includes a second tubing section 68 that communicates with the inlet 70 of a pump 72. The outlet 73 of pump 72 communicates with a tubing section 74 leading to an inlet 7a5 to the source 60. Downstream flow in tubing section 74 is indicated by the arrow 76.

To increase the exhaling rate, the flow of liquid can be reversed to flow into the outlet of the lower chamber and cause a more rapid rise in pressure in the lower chamber. By cycling this pump between forward liquid flow (out from the outlet) and reverse liquid flow (into the outlet), the inhale/exhale rate can be increased such as to mimic a lung breathing during running or other strenuous exercise. To keep the flow of fresh nutrient containing liquid cell media into the lower chamber, the forward flow cycle can be longer than the reverse flow cycle to have a net forward mass flow rate of liquid through the bottom chamber. For example, the forward flow can be for three seconds and reverse flow for two seconds. When the pump is in a pump on or first pumping state, liquid is pumped at a first rate from outlet 36 of the aspirator 8 and causes the pressure drop in the bottom chamber of the aspirator. When the pump is in a second state with the pump off or pumping at a rate that is slower than the pumping rate in the first state, or in a reverse flow direction, the membrane in aspirator 8 relaxes or moves toward the upper chamber as the pressure increases in the lower chamber (e.g. as the pressure drop in the bottom chamber is relieved). The pump can be cycled between the first and second pumping states to repeatedly cause inhaling and exhaling from the top chamber of the aspirator. In addition, the pump can be cycled between states at variable and periodic rates to mimic breathing. Also, the pumping rate can be varied, using for example, a variable speed pump, to control the amount of the pressure drop in the bottom chamber and control the volume of inhaled and exhaled gas from the top chamber. The pump can also be a reversible flow pump that can pump liquid from the outlet 36 or pump liquid into the outlet. The pump can be responsive to control signals to control the pumping flow rate, pumping direction and duration of pumping times.

Although they can be the same, the duration of forward flow and reversed, reduced and/or stop flow rate times do not need to be the same. For example, one can have forward flow for three seconds followed by stopping forward flow for five seconds; for example to allow the membrane to relax and move toward the top chamber.

Figure 4:
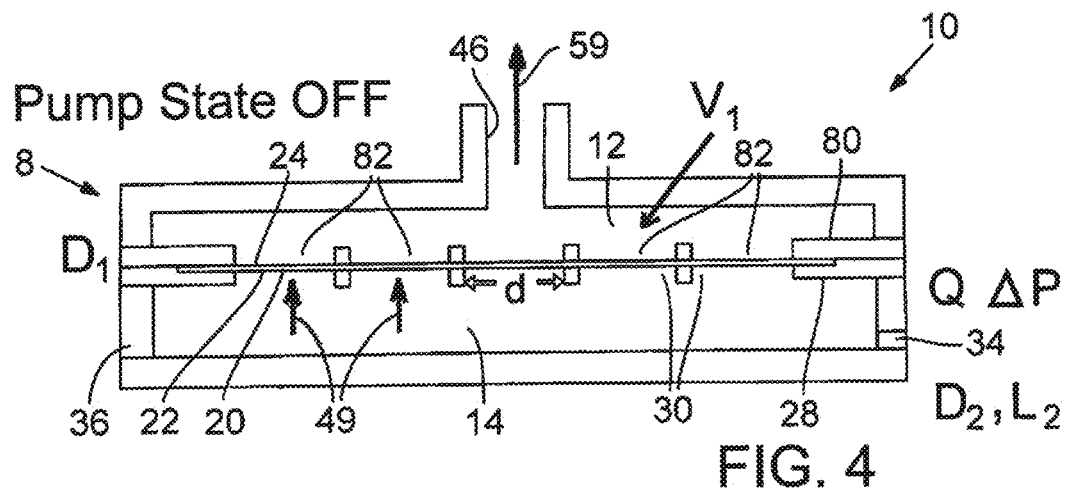
FIGS. 4 and 5 are a schematic illustrations showing cross-sectional views of an exemplary embodiment of the disclosed microfluidic aspirator indicating various parameters in a Pump OFF state (FIG. 4) and a Pump ON state (FIG. 5).
Figure 5:
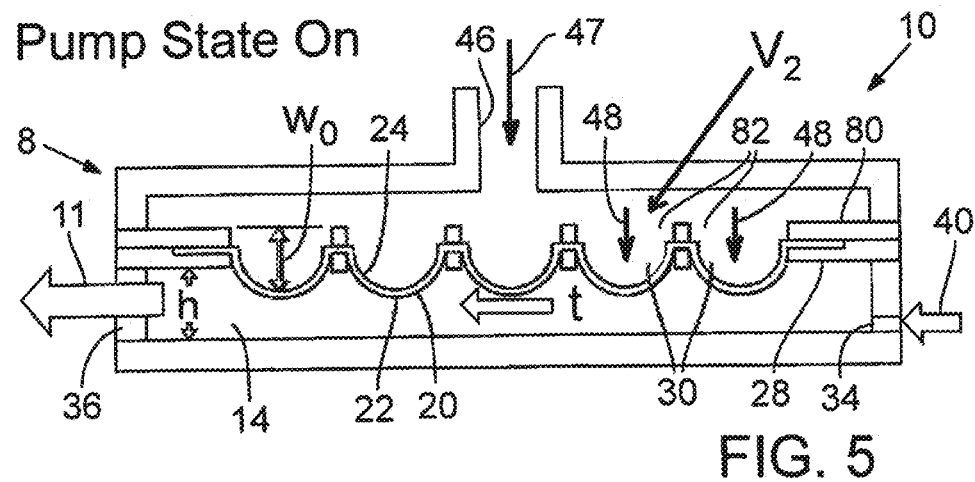

FIG. 4 is similar to FIG. 2 in that it illustrates the pump off state and FIG. 5 is similar to FIG. 1 in that it illustrates the pump on state. In FIGS. 4 and 5, an upper substrate 80 is shown between top chamber 12 and the membrane 20. The substrate 80 has one or more openings (five in the example of FIGS. 4 and 5), several of which are indicated by the number 82. The openings 82 are aligned with the openings 30 in the substrate 28, that is openings 82 overlay openings 30 at least in part, and more desirably entirely, to facilitate expansion of the membrane toward the lower chamber in the pump on state due to the reduced relative pressure in the lower chamber in comparison to the pressure in the upper chamber. In FIGS. 4 and 5, the membrane is not shown to scale as it is typically very thin such that there is no need for a recess in the top surface of the substrate 28 to accommodate the membrane and there is desirably no gap between the top surface 24 of membrane 20 and the bottom surface of substrate 80 or between the bottom surface 22 of membrane 20 and the top surface of substrate 28. This is true of other embodiments disclosed herein where the membrane is shown for convenience as having a thickness that makes it seem like a gap between the substrate surfaces and the membrane is present. However, if desired, such a gap can be provided.

Various parameters of the aspirator device are identified as follows: h=bottom chamber height in an embodiment where the bottom chamber has a constant height, such as by a plate of height h; d=diameter of openings over which membrane is stretched in the example circular openings; E (not indicated in these figures)=elasticity of membrane, which affects how fast the membrane returns to its relaxed position if pumping of liquid from the outlet is stopped; $D_1$=Diameter of outlet in the example a circular outlet; $D_2$=Diameter of inlet in the example of a circular inlet; $L_2$=Length of inlet restriction (time) in the example where the inlet restriction is formed in the housing 10 leading to the lower chamber; $V_1$=volume of the top chamber in a pump resting (off) state; $V_2$=volume of the top chamber after deflation (the pump in a pump on state); $w_0$=deflation height, the height to which the membrane expands toward the lower chamber; Q=flow rate; $\Delta P$=pressure drop caused by restriction of fluid flow; $\tau$=shear stress on the membrane; and f=frequency of pumping (e.g. the cycling rate between off and on states). These use of these variables is explained below.

In some examples, $D_1$ is greater than $D_2$, where the restriction is in the inlet. Thus, in some embodiments, the ratio of $D_1/D_2$ is greater than 1 (such as 1.1-50, 1.5-10, 2-15, 3-20, 4-25, 5-30, 8-40, or 10-50), for example, about 2, 3, 4, 5, 6, 7, 8, 9, 10, 12, 15, 20, 25, 30, 35, 40, 50, or more. In one non-limiting example, the ratio of $D_1/D_2$ is about 10. In embodiments where the inlet and/or outlet are not circular in cross-section and the restriction is at the inlet, the ratio of the cross-sectional area of the outlet to the cross-sectional area of the inlet is greater than 1 (such as 1.1-50, 1.5-10, 2-15, 3-20, 4-25, 5-30, 8-40, or 10-50), for example, about 2, 3, 4, 5, 6, 7, 8, 9, 10, 12, 15, 20, 25, 30, 35, 40, 50, or more. A ratio of 10 to 1 is one specific example. These same ratios desirably apply to the total cross sectional area of all outlets to the total cross sectional area of all inlets and also desirably apply to the ratio of the cross sectional area of all outlets to the cross sectional area of a restriction located upstream of the aspirator 8, for example in a liquid supply line upstream of the inlet. The pressure drop is in general proportional to the ratio of the total cross sectional area of all outlets to: (a) the total cross sectional area of all inlets if the restriction is included at the inlet; or (b) the cross sectional area of the restriction if upstream from the inlet. The higher the ratio, the larger the pressure drop in response to a given flow rate, and also the larger the deflection of the membrane for a given flow rate. The port in the top chamber can be eliminated if desired.

Figure 6:
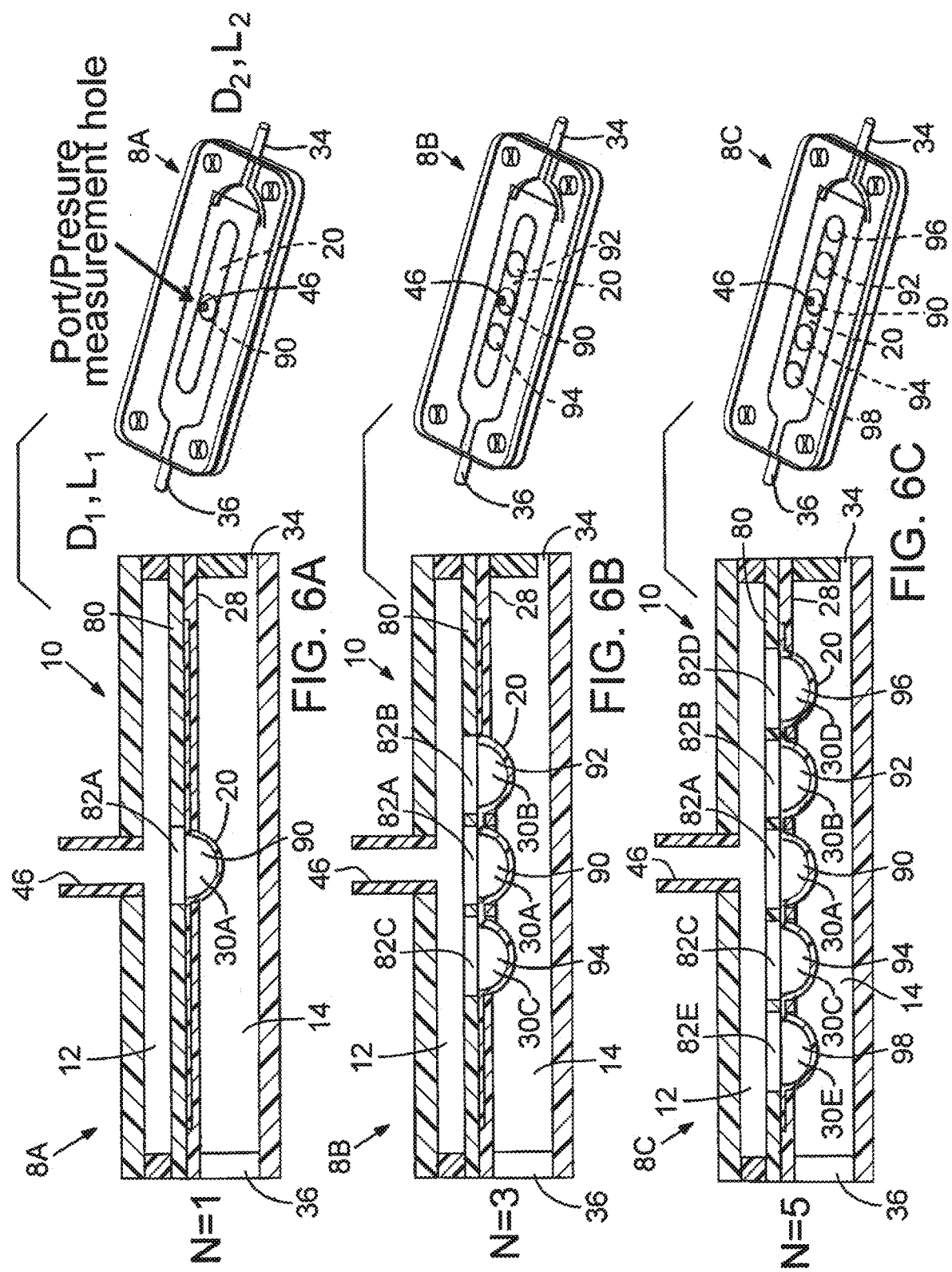
FIGS. 6A-6C are a series of schematics illustrations of exemplary cross-sectional (left) and perspective (right) views of embodiments with increasing numbers of membrane expansion wells and increasing membrane expansion surface area, such as one well (FIG. 6A), three wells (FIG. 6B), and five wells (FIG. 6C). The wells comprise membrane-covered openings between top and bottom chambers. In the cross-sectional views of these embodiments, the port in the top chamber is not shown in the cross sectional views for convenience, but may be present (for example, as shown in the perspective views of each of these FIGS.).

FIGS. 6A, 6B and 6C illustrates three exemplary aspirator apparatus embodiments; respectively with increasing membrane expansion surface area. Numbers for elements in these FIGS. that correspond to the numbers in FIGS. 1, 2 4 and 5 have been included in FIGS. 6A-6B and will not be discussed further. In some cases a letter has been added to an element for convenience in describing the embodiments (e.g. 30A corresponding to an opening 30 in FIG. 1, 2, 3 or 4).

The exposed membrane surface area is a function of the number of openings in the substrate between the top and bottom chambers, and also the size of the openings. In the embodiments shown in FIGS. 6A-6C, the aspirator respectively includes 1, 3, or 5 membrane-covered openings or wells. The single well 90 of the aspirator of FIG. 6A is defined by openings 30A and 82A in the respective substrates 28 and 80. The three wells 90, 92 and 94 of the aspirator of FIG. 6B are respectively defined by openings 30A, 82A; 30B, 82B; and 30C, 82C in the substrates 28, 80. The five wells 90, 92, 94, 96 and 98 of the aspirator of FIG. 6C are respectively defined by openings 30A, 82A; 30B, 82B; 30C, 82C; 30D, 82D; and 30E, 82E in the substrates 28, 80. However, any number of openings can be utilized, such as 1-50 openings or more, with a 96 well or opening device being one desirable example. Other examples include 1-10, 3-12, 5-15, 10-20, 15-30, 25-40, or 30-50 openings. In other examples, the device includes more than 20 openings (such as more than 50, more than 100, more than 200, more than 400, more than 500, or more. In some non-limiting examples, the devices include 1, 3, 5, 8, or 16 openings; however, any number of openings can be selected, depending on the size of the device and the particular use. In addition, the openings can be arranged in any configuration, such as linearly, in a grid, circularly, radially, or other arrangements, such as in a bronchial or branched pattern.

The size of the openings can be selected based on the desired use of the device. In some embodiments, the openings are about 1-100 µm in diameter (such as about 1-10, 3-15, 5-20, 10-50, 25-60, 40-80, or 50-100 µm diameter). In other examples, the openings are more than 100 µm in diameter, such as 200 µm, 400 µm, 500 µm, 750 µm, 1 mm, 2 mm, 4 mm, 5 mm, 10 mm, 20 mm, or more in diameter. One specific example is 4 mm. In addition, while round (circular) openings are used in some exemplary embodiments illustrated herein, other shapes, including oval, square, rectangular, or other shapes can also be used.

The membranes 20 utilized in the disclosed devices are flexible, and in some examples, porous (for example, to permit diffusion of nutrients from the liquid chamber to cells located on the air chamber side of the membrane). In some embodiments, the membrane material is an elastic, polymeric material capable of resilient deformation and reformation (e.g., such as expanding to form a semi-sphere and contracting back to its original shape, or resting state, such as the shape it retains when no external force is exerted on the material to force it to expand). The material, however, should not be so elastic as to lose its shape over an extended period of time (e.g., time periods ranging from hours to days to weeks to months). In some non-limiting examples, the membranes are polyurethane polydimethylsiloxane (PDMS), latex, or rubber membranes. However, any material suitable for thin membranes can be used, including poly-L-lactic acid, polycaprolactone (PCL), PLLA-PCL copolymer, polyester, polycarbonate, or a combination thereof.

In some examples, the thickness of the membrane ranges from 1 to 100 µm, such as 1 to 50 µm, or 1 to 10 µm. In exemplary embodiments, the membrane is about 10 μm thick with 10 μm and 35 μm thick membranes being specific examples. In examples where the membrane has pores, such as to provide nutrients to cells supported by (associated with) the membrane, the diameter of the pores of the membrane have diameters that can range from 0.4 to 12 μm, such as 0.4 to 3 μm, or 0.4 to 1 μm, with pore densities ranging from $1\times10^5$ to $1\times10^8$ pores/cm$^2$, such as $4\times10^5$ to $4\times10^6$ pores/cm$^2$, or $2\times10^6$ to $4\times10^6$ pores/cm$^2$. In exemplary embodiments, the pores have a diameter of about 3 μm. The term about when used in this disclosure includes values within plus or minus five percent of the stated value. The membrane may be pore free, such can be the case in examples where the device is being used in viscosity and flow rate determinations and vacuum pump applications.

Figure 7:
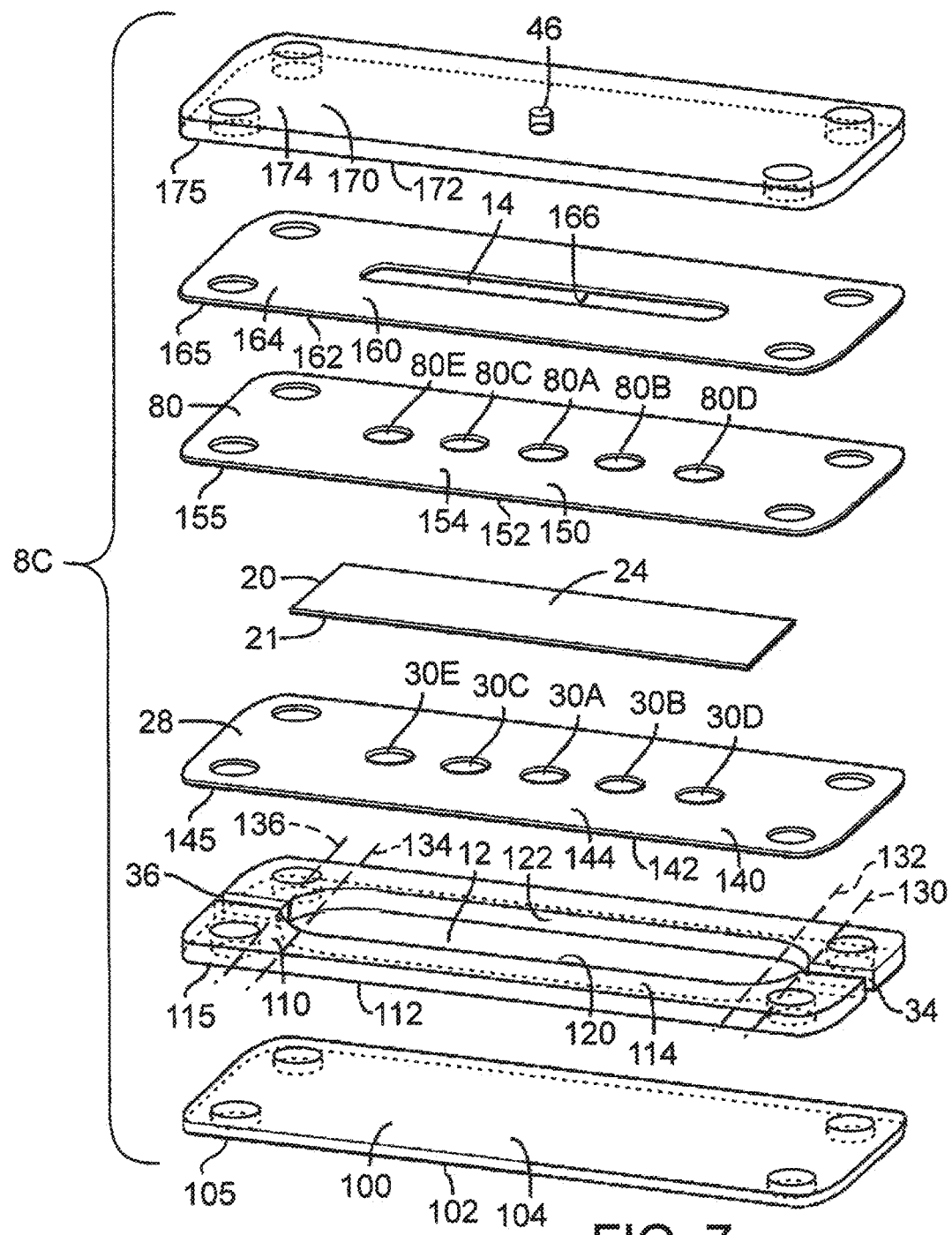
FIG. 7 is an exploded view of an exemplary aspirator apparatus of the form shown in FIG. 6.C showing the layers (also referred to as substrates) used to make this exemplary device.

FIG. 7 is an exploded view of an exemplary device like that of FIG. 6C made by stacking or laminating a plurality of substrates (also referred to as layers). The other embodiments can also be made in the same manner. The substrates making up the various layers can be in the form of plates with opposed major surfaces and side edges that are stacked and held in place by adhesive, registration pins or otherwise secured together. More or fewer substrates that those shown in FIG. 7 can be included in the aspirator, such as additional intermediate plates or substrates.

In the embodiment of FIG. 7, the apparatus comprises a bottom chamber bottom wall substrate 100 with opposed top and bottom surfaces 102, 104 and a peripheral side edge 105. The top surface 104 bounds or closes the bottom of the bottom chamber 14 in this example.

The embodiment of FIG. 7 also comprises a bottom chamber intermediate substrate 110 overlaying the bottom chamber bottom wall substrate 100. The substrate 110 has a bottom surface 112, a top surface 114 and a peripheral edge 115. The bottom surface 112 is coupled to and can abut surface 104 of substrate 100 in the assembled aspirator. The substrate 110 has bottom chamber side walls 120, 122 that surround a hollow opening between the top and bottom surfaces 114, 112 that defines the side boundaries of the illustrated bottom chamber 14. The inlet 34 and outlet 36 communicate with the chamber 14 through respective end portions of the walls 120, 122 in this example.

The illustrated chamber 14 formed by plate 110 has a first section extending longitudinally from inlet 34, and more specifically from the location where inlet 34 enters chamber 14, to a location 132; a second section extending longitudinally from a location 134 to a location 136 at the outlet 36, and more specifically at the location where outlet 36 exists the chamber 14; and at least one intermediate section extending longitudinally between locations 132 and 134. The intermediate section in this example has a constant cross sectional area and underlies the membrane receiving openings in substrates positioned above the substrate 110. These sections are also shown in the FIGS. 13 and 14 embodiment, but are of a different configuration.

Figure 8:
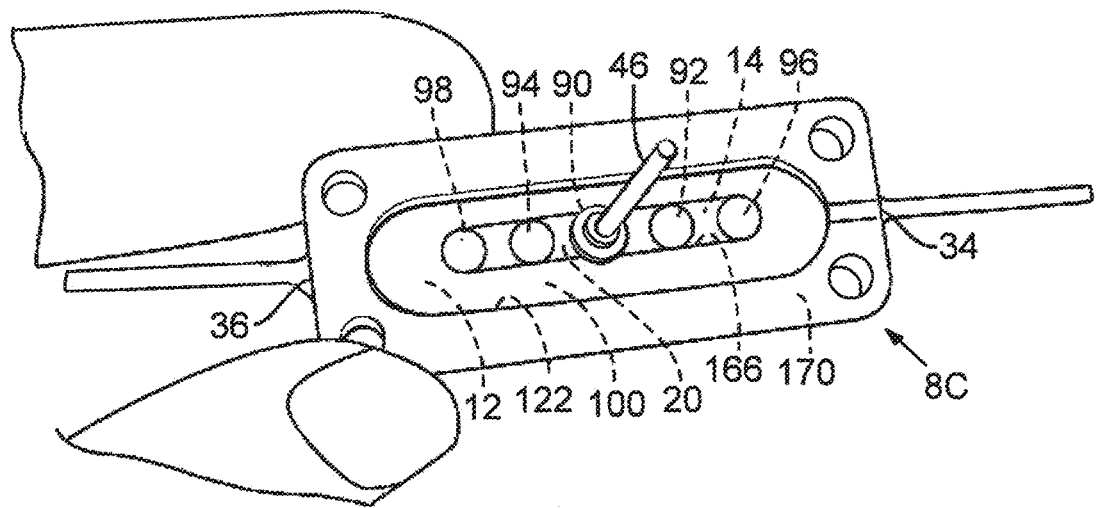
FIG. 8 is a top perspective view of a five well aspirator of FIG. 7, the five wells being visible through the top chamber in this embodiment.

In the illustrated FIG. 7 example, the cross sectional area of the first section is smaller at a first location (e.g. at location 130) than at a second location (e.g. at location 132) spaced further from the at least one inlet 34 than the first location. In addition, the cross sectional area of the second section is smaller at a third location (e.g. at location 136) than at a fourth location (e.g. at location 134) positioned further from the at least one outlet than the third location. In the embodiment of FIG. 7 (and also in the embodiment of FIGS. 13 and 14 discussed below), at least portions of the first and second side walls 120, 122 bounding the first section can diverge from one another moving away from the at least one inlet 34. In addition, in these embodiments, at least portions of the first and second side walls 120, 122 bounding the second section can converge toward one another moving toward the at least one outlet. In the embodiment of FIGS. 7 and 8, and of FIGS. 13 and 14, the cross sectional area of the first section progressively increases moving away from the inlet and the cross sectional area of the second section progressively decreases moving toward the outlet. In the FIGS. 13 and 14 embodiment, the side walls 120, 122 taper toward one another in the first section moving longitudinally toward the inlet and the side walls 120, 122 also taper toward one another in the second section moving longitudinally toward the outlet.

The illustrated side walls 120, 122 in these exemplary embodiments assist in preventing air or gas bubbles from being trapped in the chamber 14 as the chamber is filled and/or during operation of the aspirator. In addition, these side wall constructions also assist in establishing a more gradual transition in pressure changes in liquid as it enters and leaves the intermediate section.

With continued reference to FIG. 7, a bottom chamber top wall substrate 140 having bottom and top surfaces 142, 144 and a peripheral side edge 145 overlays the bottom chamber intermediate or bottom chamber defining substrate 110. The substrate 140 comprises the plurality of spaced apart openings 30A-30E positioned above the bottom chamber 14 when the aspirator is assembled. The surface 142 of substrate 140 is coupled to and can abut surface 114 of substrate 110 in the assembled aspirator. The top surface 144 of substrate 140 is positioned below and is coupled to and can engage, e.g. abut, the bottom surface 22 of the membrane 20 in the assembled aspirator with the membrane 20 overlaying the openings 30A-30E. The membrane 20 has a peripheral edge 21 extending between the bottom and top membrane surfaces 22, 24.

A top chamber bottom wall substrate 150 has bottom and top surfaces 152, 154 and a peripheral edge 155. The substrate 150 has the plurality of spaced apart openings 80A-80e overlaying and coupled to the top surface 24 the membrane and also respectively overlaying the spaced apart openings 30A-30E of the substrate 140 of the assembled aspirator.

In addition, a top chamber intermediate substrate 160 is shown that has bottom and top surfaces 162, 164 and a peripheral edge 165 the substrate 160, has a longitudinally elongated, oval in this example, top chamber 12 opening extending through the substrate and bounded or surrounded by a side wall 166. The substrate 160 is positioned to overlay substrate 150 with the top chamber 12 overlaying the openings 80A-80E in this example. When assembled, the bottom surface 160 of substrate is coupled to and can abut the top surface 154 of substrate 150. A top chamber top substrate 170, having bottom and top surfaces 172, 174 and a peripheral edge 175 overlays substrate 160 and closes the top chamber 14. The surface 172 is coupled to and can abut the surface 164 of the substrate 160. In addition, a port 46 is shown and communicates through substrate 170 and with the top chamber 40 in this example.

The apparatus in this example thus includes top layer 170 with a port 46; vacuum chamber layer 160 with top chamber 12, top substrate 150 with openings 82A-82E; membrane 20; bottom substrate 140 with openings 30A-30E; liquid chamber layer 110 with a bottom chamber 14, inlet 34, and outlet 36; and a bottom layer 100. In this embodiment, the membrane is sandwiched between a top substrate 150 and bottom substrate 140. In addition, in this embodiment the respective openings 82A-82E and 30A-30E in the top and bottom substrates are substantially aligned with one another and have substantially the same size and shape. The apparatus can also include one or more alignment holes such as shown at each corner of each layer other than the membrane in FIG. 7, which can receive registration pins to assist with proper layer alignment during assembly of the device.

FIG. 8 illustrates an assembled aspirator of FIG. 7. The layers, or a plurality of such layers on at least one side of the membrane, can be transparent so that the functioning of the aspirator can be observed externally.

Figure 9:
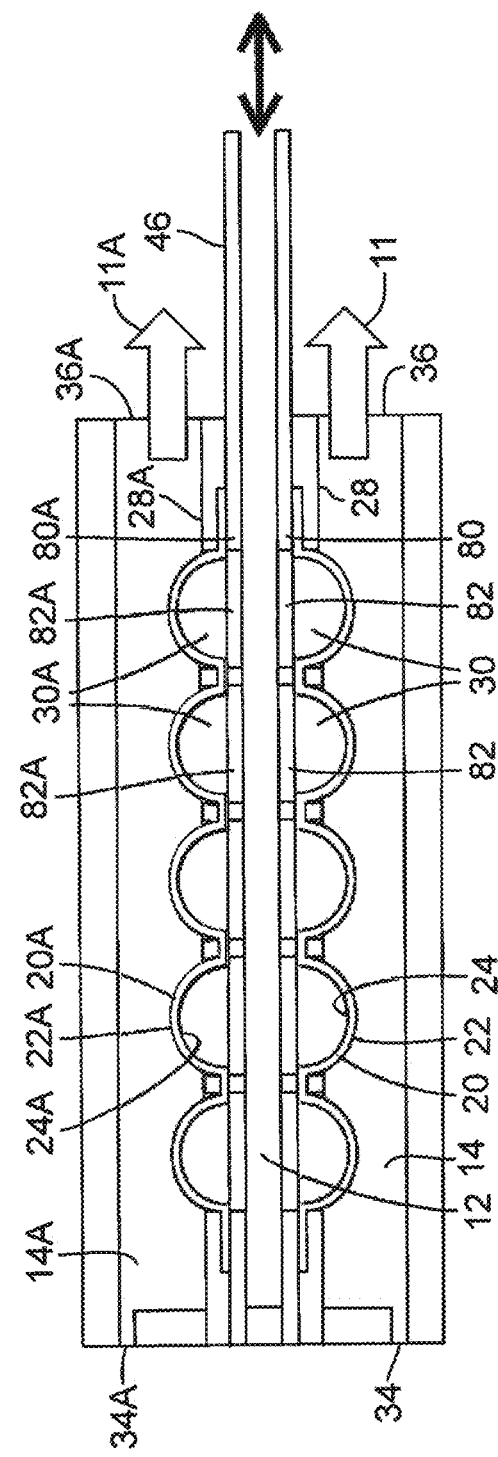
FIG. 9 shows a schematic diagram of an exemplary integrated two membrane aspirator embodiment with a central top chamber and two outer liquid flow chambers.
Figure 10:
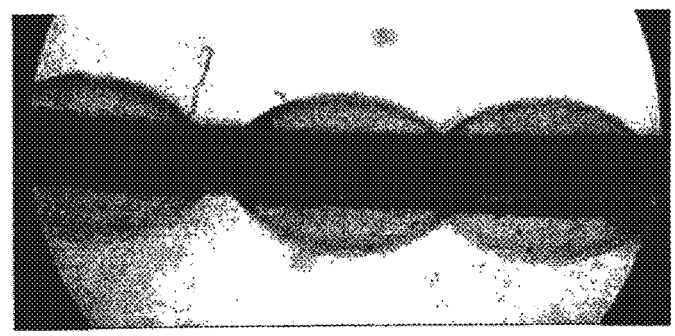
FIG. 10 is an image of the embodiment of FIG. 9 showing inflated "alveoli" supported by the membranes of this embodiment.
Figure 11:
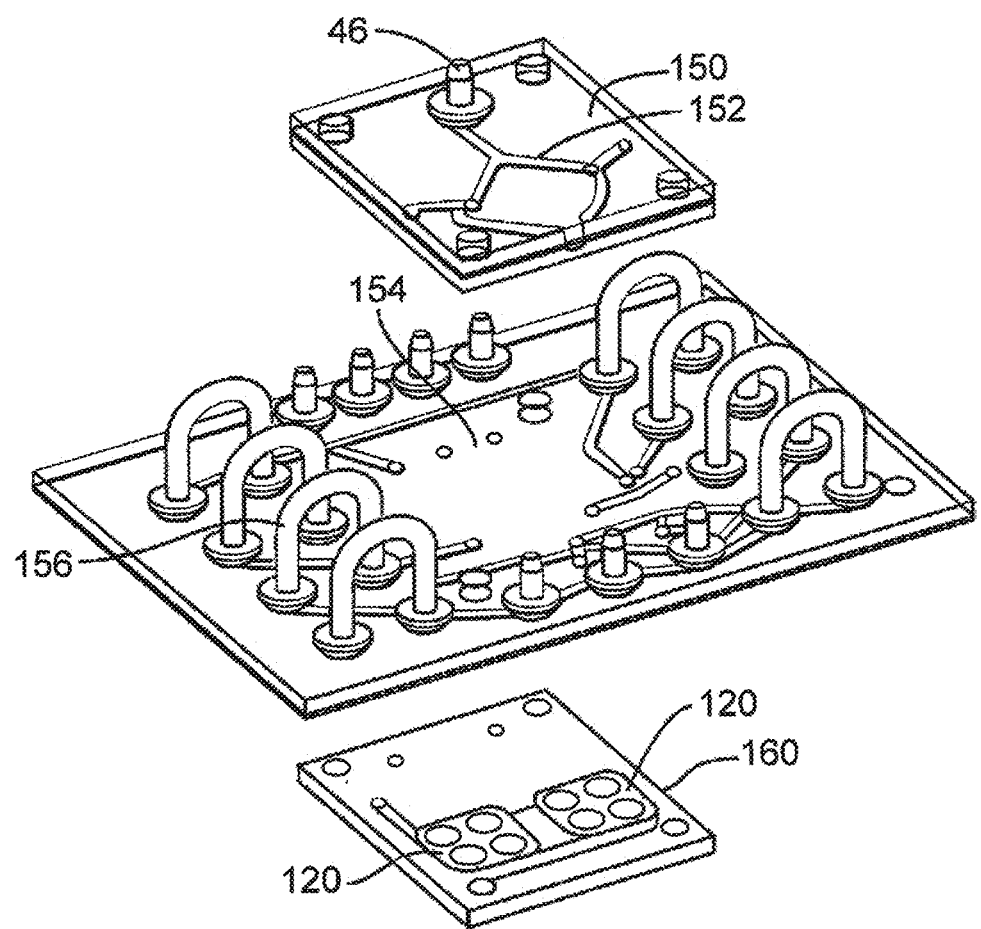
FIG. 11 is a perspective view of an exemplary lung device including an embodiment of an aspirator as disclosed herein.

In some embodiments, two of the disclosed devices can be integrated to form a device embodiment. In some examples, the devices share an air or gas chamber (referred to as the "top" chamber for example in the embodiments of FIGS. 1 and 2) and a single or common port for air or gas intake and release. An example of this construction is illustrated in FIG. 9, the device includes two liquid chambers 14, 14A, each with an inlet 34, 34A and an outlet 36, 36A. In some embodiments, the inlet 34 can be smaller in cross sectional area that the outlet 36 and the inlet 34A can be smaller in cross sectional area than the outlet 36A to provide the constriction as described above. Alternatively, the constriction can be positioned upstream of the aspirator such as, for example, in liquid supply tubing connected to the inlets. The embodiment of FIG. 9 has a single shared air or gas chamber (top chamber) 12, and a shared air or gas port 46. Elements of the lower liquid chamber in FIG. 9 are numbered as previously described, while elements of the second liquid chamber (the second bottom chamber) are given the same numbers, but with the letter A following the number. These elements will not be discussed further as they have been described above. This FIG. 9 embodiment provides a more physiologically relevant model of lung alveoli, as shown in the image in FIG. 10 of inflated "alveoli".

In various embodiments, the device can further include a plurality of cells on the surface 24 of membrane 20 facing the top chamber 12 and/or on the surface 22 of membrane 20 facing the bottom chamber 14. In some embodiments, one side of the membrane material is associated with a first population of cells and the other side of the membrane material is associated with a second population of cells. The first population of cells is associated with a side of the membrane material that is fluidly coupled with top chamber 12 and the second population of cells is associated with a side of the membrane material that is fluidly coupled with bottom chamber 14. In some examples, the first population of cells includes immune responsive cells, surfactant-producing cells, or a combination thereof, and the second population of cells includes pulmonary microvascular cells. In exemplary embodiments, the first population of cells includes alveolar type 1 (AT1) cells, alveolar type 2 (AT2) cells, or a combination thereof and the second population of cells includes human lung microvascular endothelial cells, human lung smooth muscle cells, human lung fibroblast cells, monocytes, dendritic cells, or a combination thereof (such as A549 cells, H441 cells, AT1, and/or AT2 cells).

The device may further include additional components, such as a pump 72, described in connection with FIG. 3 above, for providing liquid flow through the bottom chamber or liquid flow chamber or chambers. In some examples, the device includes a pump (such as a peristaltic pump) fluidly coupled to the outlet 36 in the bottom chamber of the device. In other examples, the device is integrated into a larger microfluidic unit or system.

In some embodiments, the devices disclosed herein are integrated into a lung organ platform or system. In some examples, the disclosed device is utilized as an alveolar device that is fluidly coupled (directly or indirectly) to one or more bronchiole devices (such as a bronchiole device disclosed in International Pat. App. Publ. No. WO 2016/049363, incorporated herein by reference in its entirety). In particular embodiments, the bronchiole device is fluidly coupled to the port 46 in the top chamber 12 of the disclosed devices. A bronchiolar device includes a device or system that can be used to mimic a bronchiole airway system of a lung for use in testing for toxicity and/or efficacy of particular drugs, as well as to investigate various diseases, such as pulmonary disease. In some examples, a bronchiolar device has at least two micro-channels (a form of chambers) separated by a membrane. The topside-channel 12 can be filled with media and airway epithelial cells for cell seeding and maintenance. The one or more outlets of the bottom-side-channel 14 is connected to a pump, which can be filled with different media. When connected to an alveolar device (such as the devices disclosed herein), the topside-channel 12 is connected to the alveolar unit, whereas the bottom-side-channel is connected to the pump to provide media circulation. In some examples, a bronchiolar device includes a plurality of channels that are arranged in a branching configuration, to more closely mimic lung physiology. Exemplary bronchiolar devices are illustrated in FIGS. 8A and 8B herein, and are described in more detail in International Pat. App. Publ. No. WO 2016/049363.

Lung device or apparatus (also referred to as an alveolar device or apparatus) can incorporate aspirators as disclosed herein. One example of a lung apparatus is shown in FIG. 12. This apparatus includes a bronchiole unit 150; a branched microchannel network 152 mimicking or recapitulating branching in a human lung with a port 46, the microchannel network 152 being an exemplary top chamber 12; a multilayer microchannel network 154 for fluid management between bronchiole and alveolar units (for delivering liquid to the lower chambers of the apparatus to cause inhaling and exhaling through the port 46); valves, such as pinch valves 156, for flow switching and management to control the flow of liquid (e.g. from a source in response to pumping by a pump) to lower chambers of the device; and an alveolar device 160 of the present disclosure including membranes 20 and one or more liquid flow (bottom) chambers with respective inlets and outlets, as previously described, that can be cyclically stretched using microfluidic aspiration as described herein to breathe air or gas in/out of the port 46 of the lung apparatus.

In some embodiments, a lung organ platform includes one or more of the disclosed devices (also referred to as alveolar device(s)) fluidly coupled to one or more bronchiole devices, and one or more fluid management systems (such as a fluid circuit board disclosed in International Pat. App. Publ. No. WO 2016/049365, incorporated herein by reference in its entirety).

Another exemplary lung system including the disclosed (alveolar) devices is illustrated in FIG. 12. In this FIG. 12, the top chamber includes branches or channels 152, 153 that comprise the top chamber. These branches communicate with the top surface of membrane sections 20, with the bottom surfaces of the membrane communicating with a liquid flow chamber with respective inlets and outlets (not shown but included in substrate block 180 that can be a bottom chamber structure as previously described.

In further embodiments, the devices disclosed herein (for example when integrated in a lung organ mimetic system) can be coupled to one or more additional organ mimetic systems, such as heart devices, liver devices, kidney devices, or the like.

FIGS. 14 and 15 illustrate an aspirator with 96 wells or openings in substrates on either side of a membrane. The substrates can comprise plates. The substrates in the FIG. 14 embodiment in common with those in the FIG. 7 embodiment have been given the same numbers and will not be discussed further. In FIG. 14, the top chamber defining substrate 160 and top most substrate 170 have been omitted for clarity. In the embodiment of FIG. 14, the restriction 66 is located upstream of the inlet 34. In addition, the inlet 34 and the outlet 36 to and from the bottom chamber 14 extend downwardly through the substrates such that the port 46, inlet 34 and outlet 36 are all positioned for ready access at the same side of the aspirator. FIG. 15 illustrates the substrates of FIG. 14 in an exemplary assembled state.

Further disclosed herein are devices that can be utilized to measure or determine various physical and/or chemical products of liquids, including flow rate, viscosity, temperature, pH, ion concentration, and presence of air bubbles. The devices include a liquid chamber and an air chamber separated by a membrane component. The membrane component is deformed (e.g., into the liquid chamber or the air chamber) in response to a change in pressure created by a liquid flow restriction in the liquid chamber or upstream or downstream of a port of the liquid chamber (depending on the direction of fluid flow through the device). The pressure change is detected by a pressure sensor coupled to the air chamber and properties of the liquid can be determined based on known properties of the liquid and/or device (such as flow rate or viscosity) or standard curves.

In some embodiments, liquid flows through the liquid chamber from a first port toward a second port. A restriction is provided in the flow path, such as at the second port. The restriction (e.g., the second port) has a smaller cross sectional area than the first port. When the liquid flows into the liquid chamber from the first port toward the restriction, a pressure increase is created in the liquid chamber, causing an expansion of the membrane into the air chamber ("into" includes "toward"). A pressure sensor coupled to a port in the air chamber detects the pressure change and provides an output (for example, through an electrical connection to a computer chip or other device). In other embodiments, liquid flows through the liquid chamber from the second port toward the first port (for example, liquid is withdrawn from the liquid chamber through the first port). When the liquid flows away from the restriction, a pressure decrease is created in the liquid chamber, causing an expansion of the membrane into the liquid chamber. The pressure sensor coupled to the air port detects the pressure change and provides an output.

Figure 24A:
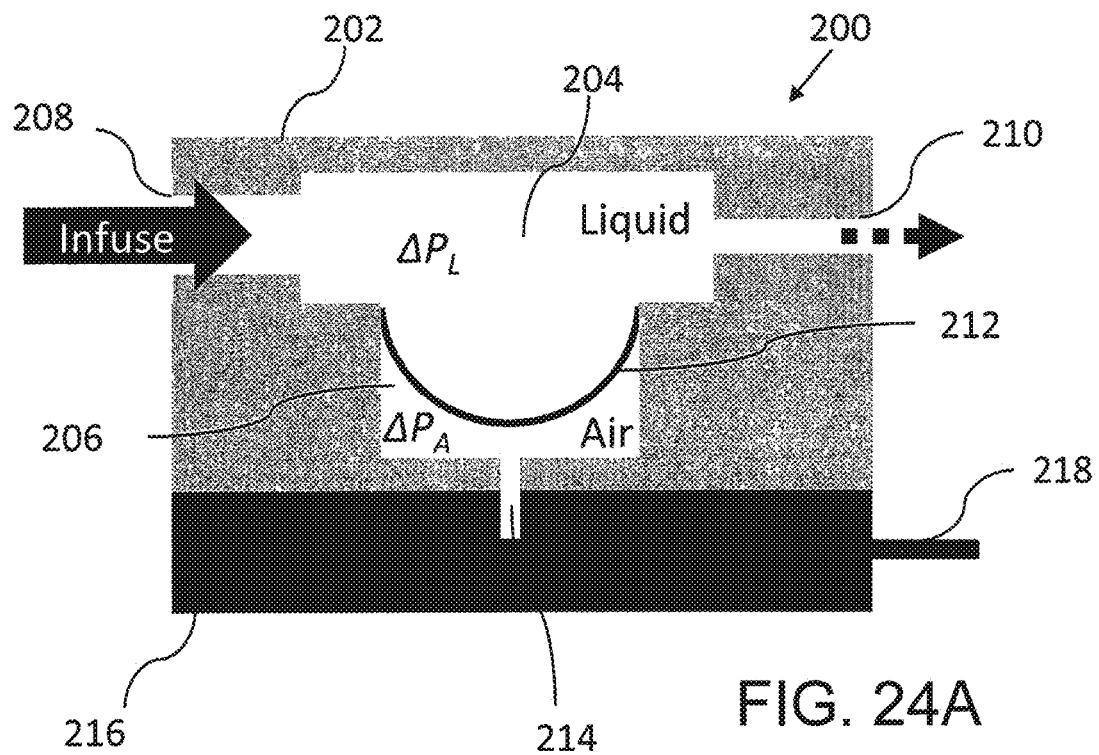
FIGS. 24A and 24B show an exemplary embodiment of the flow sensor.
Figure 24B:
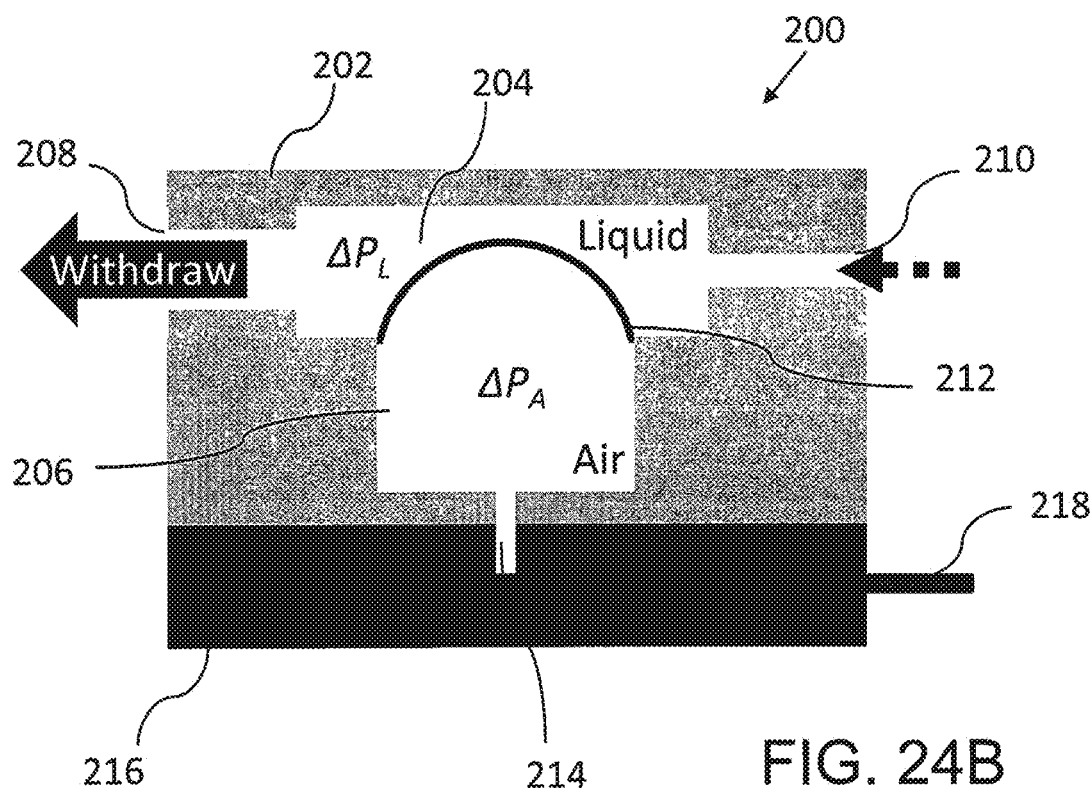
Figure 25A:
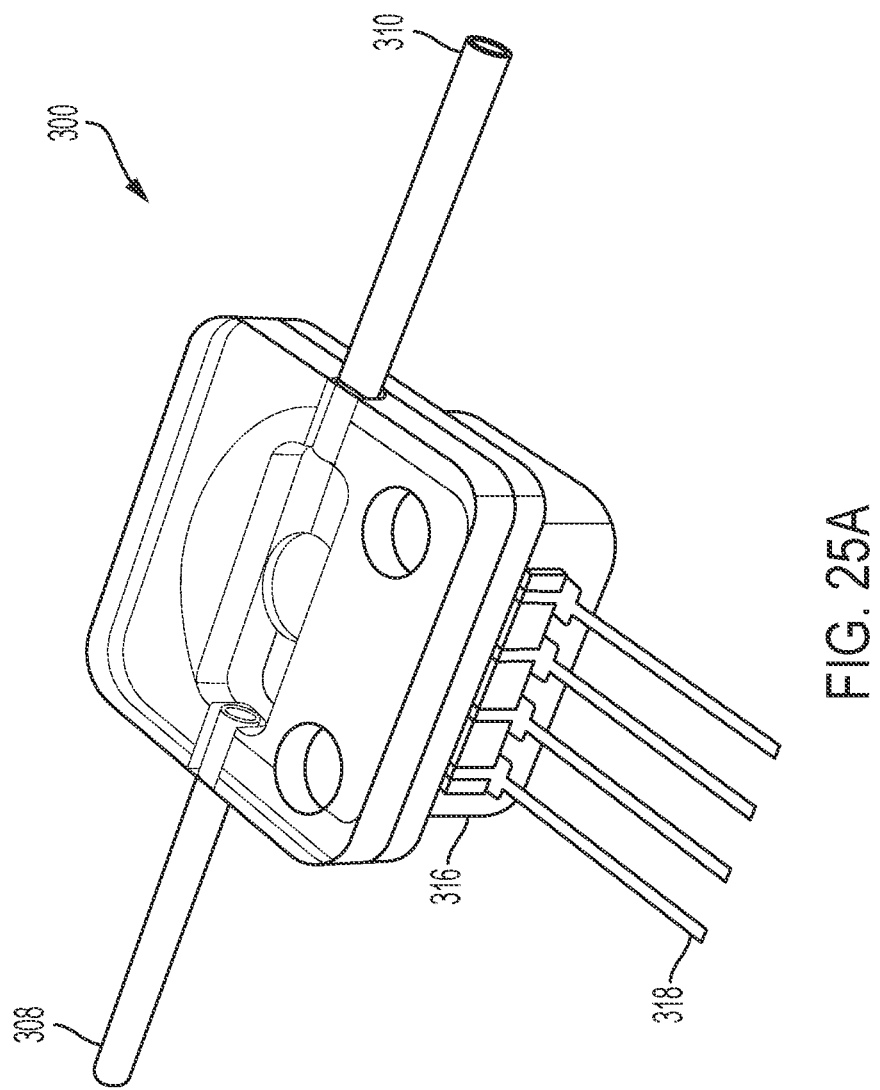

FIGS. 24A and 24B depict an embodiment of the device in the state of liquid flow toward the restriction (FIG. 24A) and away from the restriction (FIG. 24B). The device 200 includes a housing 202 having a liquid chamber 204 and an air chamber 206 and a membrane 212. The membrane includes an edge boundary and opposed first and second major side surfaces. In FIGS. 24A and 24B, the first side surface faces toward the liquid chamber, and the second side surface faces toward the air chamber. The membrane 212 is positioned between the liquid chamber 204 and the air chamber 206, the first side surface is fluidly coupled with the liquid chamber, and the second side surface is fluidly coupled with the air chamber. The terms fluidly coupled or fluidically coupled means in fluid communication with. The term fluid includes gas or liquid. In the embodiments illustrated herein, the liquid chamber is on top of (above) the air chamber. However, in other embodiments, the liquid chamber can be below the air chamber.

The device also includes at least two liquid ports in liquid chamber 204. A first port 208 is desirably located at a different side or end of liquid chamber 204 from the second port 210, for example, in a wall of the liquid chamber opposite to the second port 210. Although the embodiments illustrated herein show first port 208 and second port 210 as being substantially aligned and on opposite ends of the liquid chamber, additional configurations can be utilized including having the first and second ports on opposite sides of the liquid chamber, but not aligned with one another or having the first and second ports on adjacent sides of the liquid chamber and/or extending upwardly through the top of the liquid chamber from opposite ends of the liquid chamber. In the example of FIGS. 24A and 24B, the second port 210 is smaller (for example, in diameter or cross-sectional area) than the first port 208 and, thus, is one example of a restriction in the liquid flow path. Arrows illustrate the flow of liquid through the liquid chamber. The first and second ports may have any cross-sectional shape, including circular, rectangular, square, oval, or other shapes.

The air chamber 206 includes a port 214, which is coupled to a pressure sensor 216. As discussed herein, during flow of a liquid through the liquid chamber, a pressure change is produced due to the restriction at the second port 210, resulting in an expansion of the membrane 212 from a substantially flat state into the liquid chamber 204 or the air chamber 206, depending on the direction of liquid flow. The pressure sensor 216 includes an electrical connection 218 to provide an output, for example, to a computer or other device. In the embodiments illustrated herein, the pressure sensor is under (below) the air chamber. However, in other embodiments, the pressure sensor can be placed above or adjacent to the air chamber.

FIGS. 25A-25D illustrate a device embodiment that includes a casing for the flow sensor device. The device 300 can be enclosed in a casing 320, which includes openings that can accommodate and provide access to the first port 308 and second port 310 (or tubing connected to the first port 308 and the second port 310) and the one or more electrical connections 318 from the pressure sensor 316 to an output device.

In other embodiments, a flow restriction is provided at location outside of the second port 210, rather than the restriction being at the location of the second port. In some examples, the cross-sectional area of the first and second ports are the same or substantially the same size (e.g., cross-sectional area), and the flow restriction is created by a flow path (such as tubing) where at least a portion of the flow path has a smaller cross-sectional area than the second port. For example, the restriction can be downstream or upstream of the second port 210, depending on the direction of the fluid flow. For example, if the fluid flow is in the direction of the first port to the second port, then the restriction is downstream of the second port, while if the fluid flow is from the second port to the first port, then the restriction is upstream of the second port.

In yet further embodiments, the cross-sectional area of the first and second ports are the same or substantially the same, and the flow restriction is created by placing a porous material in the second port, for example, filling the whole diameter of at least a portion of the second port. In this embodiment, the porous material responds to one or more characteristics of the liquid flowing through the device (e.g., is a "stimulus-responsive material"), resulting in a change in the flow rate through the material. As discussed below, in some examples, the stimulus-responsive material shrinks or swells in response to a characteristic of the liquid, changing the porosity of the material and resulting in change in resistance to liquid flow. This produces the flow restriction, which results in deformation of the membrane, and detection by the pressure sensor, as in other embodiments of the device.

Figure 34:
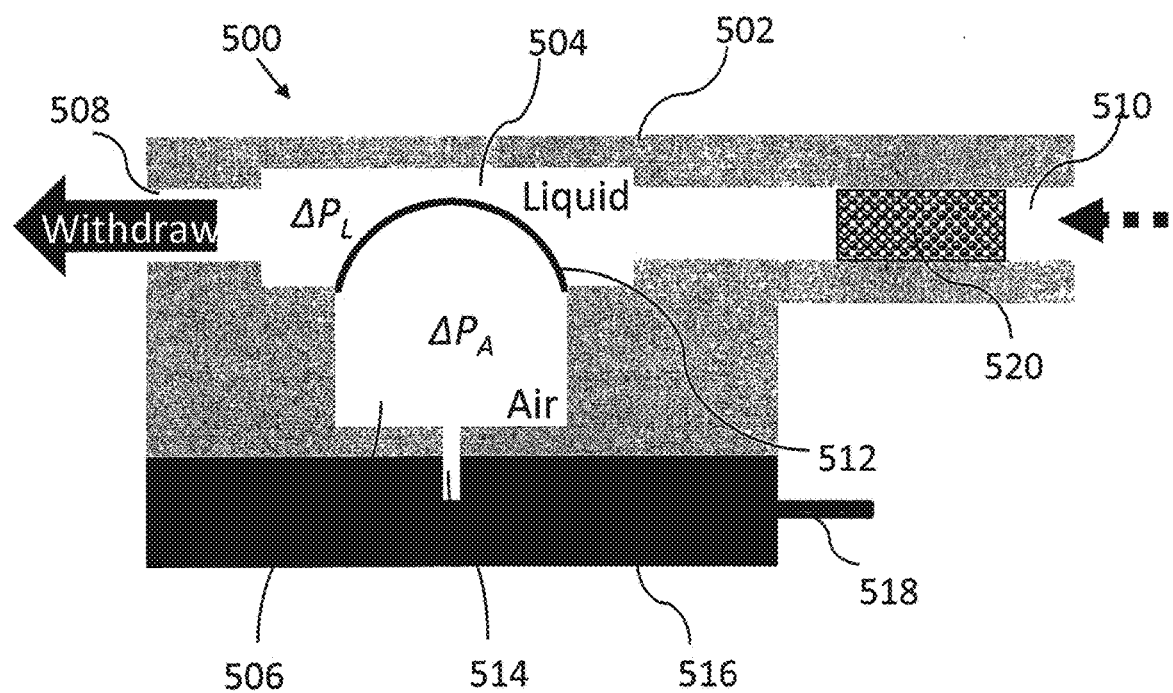
FIG. 34 shows an exemplary embodiment of the flow sensor including a stimuli-responsive bed in the second port. The schematic illustrates a state of negative pressure in the liquid chamber generated by withdrawing liquid from the first port, resulting in deflection of the membrane into the liquid chamber. Arrows indicate the direction of liquid flow.

FIG. 34 illustrates an embodiment of the device 500 that includes a housing 502 having a liquid chamber 504 and an air chamber 506 and a membrane 512. The membrane includes an edge boundary and opposed first and second major side surfaces. In FIG. 34, the first side surface faces toward the liquid chamber and the second side surface faces toward the air chamber. The membrane 512 is positioned between the liquid chamber 504 and the air chamber 506, the first side surface is fluidly coupled with the liquid chamber, and the second side surface is fluidly coupled with the air chamber. The air chamber 506 includes a port 514, which is coupled to a pressure sensor 516. The pressure sensor 516 includes an electrical connection 518 to provide an output, for example, to a computer or other device.

The device also includes at least two ports in liquid chamber 504. A first port 508 is desirably located at a different side or end of liquid chamber 504 from the second port 510, for example, in a wall of the liquid chamber opposite to the second port 410. Although the embodiments illustrated herein show first port 508 and second port 510 as being substantially aligned and on opposite ends of the liquid chamber, additional configurations can be utilized, including having the first and second ports on opposite sides of the liquid chamber, but not aligned with one another or having the first and second ports on adjacent sides of the liquid chamber and/or extending upwardly through the top of the liquid chamber from opposite ends of the liquid chamber. In the example of FIG. 34, the second port 510 is the same or substantially the same size (for example, in diameter or cross-sectional area) as the first port 508. Second port 510 includes a stimulus-responsive semi-porous material 520 (such as a packed bed). Arrows illustrate the flow of liquid through the liquid chamber. The first and second ports may have any cross-sectional shape, including circular, rectangular, square, oval, or other shapes.

In some embodiments, the stimulus-responsive material 520 is responsive to one or more physical and/or chemical properties of a liquid, such as temperature, pH, and/or ion concentration. For example, the material may swell or shrink in response to one or more properties of the liquid, resulting in an increase or decrease in the flow restriction. In some examples, the stimulus-responsive material is a pH-sensitive polymer (for example, a polyacid (or anionic polymer), a polybase (or cationic polymer), or a hydrogel). In other examples, the stimulus-responsive material is an ion exchange resin. In further examples, the stimulus-responsive material is a thermo-responsive polymer. In other examples, the stimulus-responsive material is responsive to more than one stimulus. For example, the material may be a co-polymer that is responsive to both temperature and pressure. In each example, the material has a known response (e.g., swelling or shrinking) in response to a particular characteristic (such as pH, temperature, or concentration or type of ion).

Various parameters of the devices disclosed herein are identified as follows: h=liquid chamber height in an embodiment where the liquid chamber has a constant height; d=diameter of opening over which membrane is stretched; E=elasticity of membrane; D1=Diameter of first port in liquid chamber; D2=Diameter of second port in liquid chamber; D3=diameter of flow restriction when flow restriction is outside of the second port; Q=flow rate; $\Delta$P=pressure drop caused by restriction of fluid flow; $\mu$=fluid viscosity; and f=frequency of pumping (e.g., the cycling rate between off and on states). The use of these variables is explained below.

In some examples, D1 is greater than D2, where the restriction is in the second port. In other examples, D1 is greater than D3, where the restriction is outside the second port. Thus, in some embodiments, the ratio of D1/D2 or the ratio of D1/D3 is greater than 1 (such as 1.1-50, 1.5-10, 2-15, 3-20, 4-25, 5-30, 8-40, or 10-50), for example, about 2, 3, 4, 5, 6, 7, 8, 9, 10, 12, 15, 20, 25, 30, 35, 40, 50, or more. In one non-limiting example, the ratio of D1/D2 or the ratio of D1/D3 is about 10. In embodiments where the first and second ports are not circular in cross-section and the restriction is at (or in) the second port, the ratio of the cross-sectional area of the first port to the cross-sectional area of the second port or the flow restriction outside of the second port is greater than 1 (such as 1.1-50, 1.5-10, 2-15, 3-20, 4-25, 5-30, 8-40, or 10-50), for example, about 2, 3, 4, 5, 6, 7, 8, 9, 10, 12, 15, 20, 25, 30, 35, 40, 50, or more. A ratio of 10 to 1 is one specific example. The pressure drop is in general proportional to the ratio of the cross sectional area of the first port to: (a) the total cross sectional area of the second port if the restriction is included at (or in) the second port; or (b) the cross sectional area of the restriction if outside of the device. The higher the ratio, the larger the pressure change in response to a given flow rate and also the larger the deflection of the membrane for a given flow rate.

The membrane utilized in the disclosed devices is flexible. In particular embodiments, the membrane is substantially non-porous. In some embodiments, the membrane material is an elastic, polymeric material capable of resilient deformation and reformation (e.g., such as expanding to form a semi-sphere and contracting back to its original shape, or resting state, such as the shape it retains when no external force is exerted on the material to force it to deform). The material, however, should not be so elastic as to lose its shape over an extended period of time (e.g., time periods ranging from hours to days to weeks to months). In some non-limiting examples, the membranes are polyurethane, polydimethylsiloxane (PDMS), polyvinylidene difluoride, latex, or rubber membranes. However, any material suitable for thin membranes can be used. In some examples, the thickness of the membrane ranges from 1 to 100 $\mu$m, such as 1 to 50 $\mu$m, or 1 to 10 $\mu$m. In exemplary embodiments, the membrane is about 10 $\mu$m thick with 10 $\mu$m and 35 $\mu$m thick membranes being specific examples.

In one non-limiting example, the pressure sensor is a Honeywell® HSCSSNN001PD2A3 pressure sensor. In some examples, the pressure sensor is a microfluidic scale pressure sensor. However, any suitable pressure sensor can be utilized in the disclosed devices, for example, pressure sensors available from Honeywell® (Morristown, N.J.) or Panasonic® (Ottobrunn, Germany). In some embodiments, the pressure sensor can detect pressures from −2 to +2 psi (for example, −1.5 to +1.5 psi, −1 to +1 psi, or −0.5 to +0.5 psi).

In other embodiments, the device does not include a pressure sensor. In these embodiments, the membrane includes an antenna that can wirelessly provide output regarding membrane deformation, for example, to an external radio frequency (RF) probe, and therefore, a pressure sensor is not required. The antenna may be integrated into or placed on the surface of the membrane. In some examples, the antenna is a metamaterial inspired antenna (see, e.g., Azad et al., *Appl. Physics Lett.* 110:224101, 2017). In particular examples of this embodiment, the device is used with an infusion pump, for example, for use during administration of intravenous fluids to a subject.

In additional embodiments, the disclosure relates to systems including the flow sensor devices provided herein. The systems can include liquid in the liquid chamber of the device. In some examples, the liquid is water or cell culture medium, but any liquid can be used. In addition, the systems can include components for moving liquid through the system (such as a liquid reservoir and a pump), connectors between the device and other components (such as tubing, channels, and/or electrical connectors), and one or more electronic modules (such as a computer) that receive and/or process data from the pressure sensor.

Figure 29:
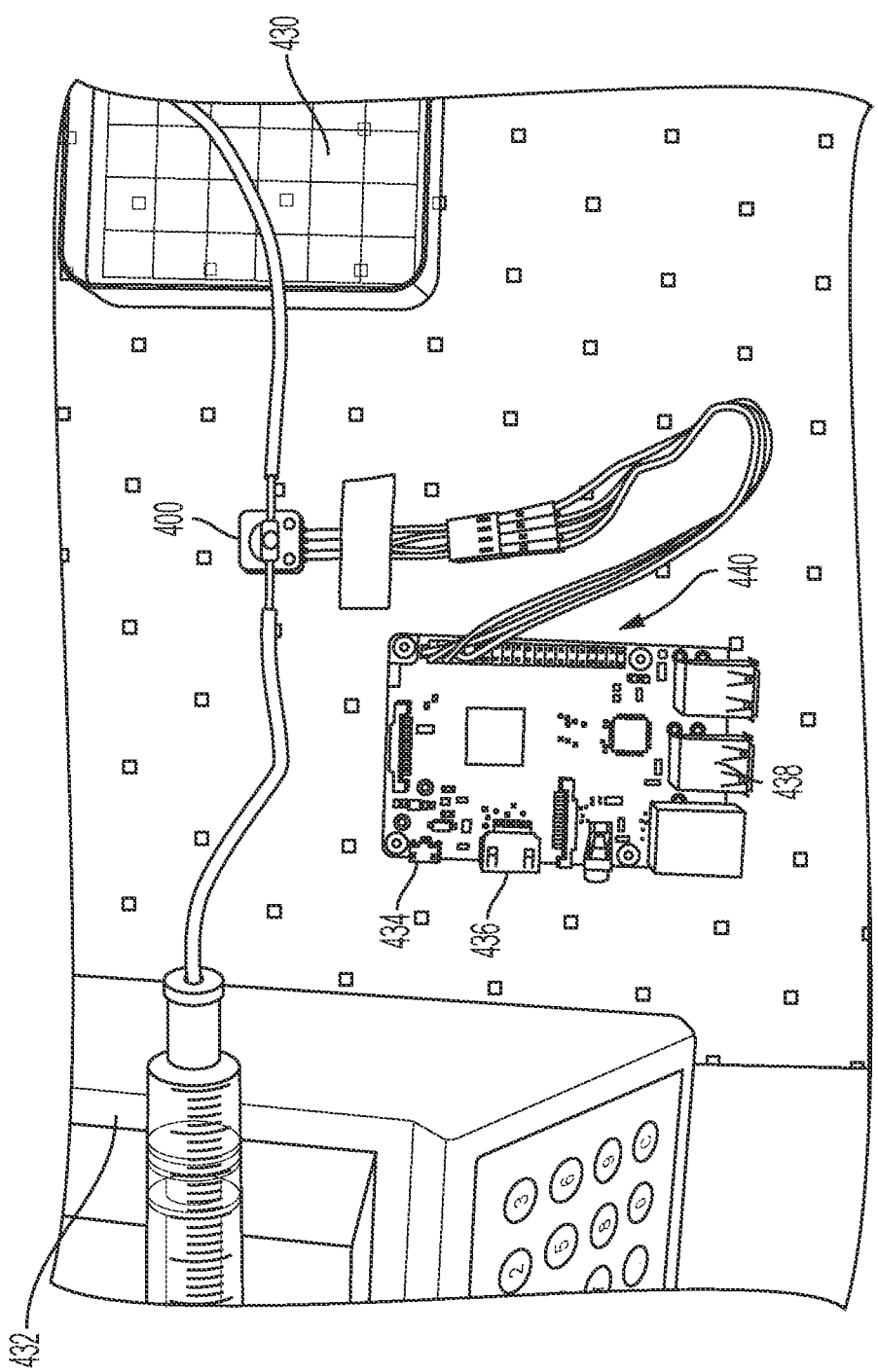
FIG. 29 is a digital image of an embodiment of a system including a flow sensor device coupled to a reservoir, a syringe pump, and a Raspberry Pi computer.

FIG. 29 depicts an exemplary system including a device in accordance with this disclosure, such as the flow sensor 400. In FIG. 29, the first port is coupled to a pump 432 and the second port is coupled to a fluid reservoir 430, for example, using tubing in the illustrated embodiment. The fluid flow path can be from the pump 432 through the flow sensor 400 toward the reservoir 430 or from the reservoir 430 through the flow sensor 400 toward the pump 432. The flow sensor 400 is connected to an electronic module 440 (such as a computer) that receives information from the pressure sensor in the device and provides an output. In FIG. 29, electronic module 440 is a Raspberry Pi module, including inputs and outputs, such as a power port 434, an HDMI port 436, and a keyboard/mouse port 438.

FIG. 29 illustrates an embodiment where the pump 432 is a syringe pump. However, any type of liquid pump can be used in the systems disclosed herein. Additional types of pumps of used in the disclosed systems include peristaltic pumps, such as rotary peristaltic pumps, infusion pumps, piston pumps, or pneumatic pumps. The pumps can be miniaturized, such as micropumps or nanopumps. FIG. 29 also illustrates an embodiment where the electronic module 440 is a Raspberry Pi board. However, any type of electronic module, such as any type of computer, can be used. In some examples, the system may include one or more additional electronic modules connected to the flow sensor device, which can be used to set operating conditions, such as flow rate or to stop and start flow. These parameters can be manually, semi-automatically, or automatically controlled.

In further embodiments, the system can include additional components such as fluid management system(s) or circuit(s), pump(s), valve(s), tubing, connectors, and/or reservoirs. In some examples, the disclosed devices or systems are incorporated into a larger system or apparatus, including but not limited to fluid circuits or organ devices (such as organ-on-a-chip systems). Exemplary fluid circuits and organ devices are described in International Pat. App. Publ. Nos. WO 2016/049363 and WO 2016/049365, and U.S. Pat. App. Publ. Nos. 2017/0298966 and 2018/0066220, each of which are incorporated by reference in their entirety.

III. Methods of Making the Devices

Disclosed herein are embodiments of methods for making the devices disclosed herein. In some examples, the methods include combining one or more components disclosed herein. In addition, methods of making the membranes utilized in the devices are disclosed.

In some embodiments, the disclosed devices are made using a plurality of substrates stacked on top of one another. At least one of the substrates is configured to accept a one or more inlets, outlets, or ports, for example for introducing or removing liquid and/or air or gas. For example, as illustrated in FIG. 7, a plurality of substrates, including top substrate (layer) 170, vacuum chamber substrate (layer) 160, top membrane frame (substrate) 150 with openings 82A-E, bottom membrane frame (substrate) 140 with openings 30A-30E, liquid chamber substrate (layer) 110, and bottom substrate (layer) 100. In some embodiments, a membrane is sandwiched between two membrane frames or substrates and the membrane frames and membrane are incorporated into the device as a unit. For example, in some embodiments, membrane 20 is sandwiched between the two membrane frames or substrates 140, 150 and the membrane frames and membrane are incorporated into the device as a unit. The inlets, outlets, and ports of the substrates can be formed, for example, using a laser. In particular disclosed embodiments, one or more tube lines are attached, such as by using an adhesive, to the inlet and outlet of the liquid chamber layer. The tube lines can be attached at any point during making the device. The substrates are coupled together, for example using an adhesive or adhesive tape (single-sided and/or double-sided) and lamination or fasteners. In some examples, the device is assembled on an alignment stage, which includes one or more posts or pins that pass through the one or more alignment holes in each substrate to provide proper alignment of the components of each substrate or layer during assembly.

The substrates can be made of any suitable polymeric material capable of being fabricated to include the particular components of the disclosed devices, such as chambers and ports. For example, in the case of an exemplary lung device, any suitable polymeric material can be used that is capable of being fabricated to include the particular components of the bronchiolar device, such as channels, inlets, outlets, and chambers. In particular disclosed embodiments, the substrates include a polymer material, such as polydimethylsiloxane (PDMS), acrylic, polycarbonate, polyethylene terephthalate (PET), PET-G, Kapton, and/or polyether ether ketone (PEEK) materials. Each substrate can be made of the same or different material as each other substrate used in the device.

Additional methods of making the devices can be utilized, for example, by separately fabricating top and bottom chambers and assembling them with a membrane between the chambers and/or by separately fabricating liquid and air chambers and assembling them with a membrane between the chambers. The membrane can be fabricated as a separate layer and incorporated during device assembly or can be assembled as a unit with the top and bottom membrane frame substrates, for example to facilitate membrane handling (decreasing the risk of damage and facilitating additional manipulations, such as sterilization). In one embodiment, the membrane is placed on a first membrane frame including the desired number of openings, such as one opening or more than one openings. A second membrane frame, with the same number of openings (such as one opening or more than one openings) is placed over the membrane with the opening(s) in the first (bottom) membrane frame and the opening(s) in the second (top) membrane frame being aligned. In some examples, the membrane is produced by spin coating; however, other techniques, such as spray coating, extrusion, or blown bubbles can also be utilized. In some examples, the membrane between the membrane frames includes a plurality of pores. In other examples, the membrane between the membrane frame is not initially porous and a plurality of pores are introduced in the membrane (for example, using a laser) prior to incorporating the membrane and membrane frames into the device.

One challenge of integrating membranes into microfluidic devices involves the difficulty of placing and fixing flexible membranes into planar systems. Although thin membranes can be fabricated in situ and assembled in a device, it is not trivial to integrate flexible membranes using common fabrication techniques available for microfluidics. Typically, membranes (such as PDMS membranes) are molded on a glass or silicon substrate. To remove a thin membrane from the substrate and incorporate it into a microfluidic device requires precise handling. The bonding between the substrate and the thin elastic membrane can be so strong that it makes the peeling step a challenge. Once the membrane is peeled off from the substrate, thin membranes (less than 50 µm) tend to crumple together and it is difficult to stretch the membranes back to their original state. These handling and fixation issues may decrease yield of usable membranes, cause instability, and eventually affect the function of the device in which it is incorporated. To address these challenges, in some examples, an exemplary method based on a combination of laser based micro-patterning and lamination techniques can be used to make the membranes and put them in a frame. This technique can allow peeling off the membrane from the substrate rapidly and easily using an adhesive layer or solvent (such as an alcohol), transporting the membrane with a membrane holder layer (e.g., a membrane frame) and the simpler and more effective integration of the membrane into the microfluidic device.

Thus, in some embodiments, a thin membrane (such as a polyurethane or PDMS membrane) is produced on a solid substrate using a spin coating technique. The membrane is peeled off the substrate, using water and/or alcohol (such as ethanol) to facilitate release of the membrane from the substrate and to reduce tearing. The membrane is placed on a second solid substrate and flattened and/or smoothed out. The membrane can then be transferred to a substrate that includes openings (such as a substrate 28, comprising one form of a substrate frame, with openings 30), for example, by placing the substrate or membrane frame on the membrane and lifting it from the solid substrate. If two membrane frames are used, a second membrane frame is aligned with the first membrane frame and placed over the membrane, sandwiching the membrane between the two frames. In examples where a porous membrane is desired, pores can be introduced in the membrane after transfer to the frame(s), for example using electromagnetic ablation, for example with a laser.

In some embodiments, a plurality of one or more types of cells is seeded on one or both sides of the membrane. In some examples, the cells are seeded on the membrane after assembly of the device (for example, by introducing cells into the device through one or more of the inlet or outlet of the bottom chamber and/or the port of the top chamber). In other examples, cells are seeded on one or both sides of the membrane prior to device assembly (for example, before or after the membrane is placed between the membrane frames).

IV. Methods of Using the Devices

The disclosed devices have numerous uses. In some embodiments, the devices are utilized as a model of lung alveolar function, or are integrated into a platform or system that mimics or models lung function. In other embodiments, the devices can be used in any application where formation of a vacuum is desired, for example with or without a port 46. In other embodiments, the devices are utilized to measure liquid flow rate, presence of bubbles in a liquid, liquid viscosity, liquid temperature, liquid pH, and/or concentration of one or more ions in a liquid. Finally, the disclosed devices can be used r in tunable lens applications.

A. Alveolar or Lung Models

In some embodiments, the disclosed devices are used to independently model alveolar function and/or lung function (for example, as an alveolar component integrated into a lung model or platform). In some examples, the disclosed devices include a plurality of cells on one or both sides of the membrane, such as alveolar cells. The bottom chamber is filled with liquid (for example, substantially or completely filled with liquid). Liquid is flowed through the bottom chamber, creating a pressure drop due to the smaller size of the inlet than the outlet. This creates a vacuum in the top chamber causing air or gas intake into the top chamber through the port, and deformation of the membrane(s) into the liquid in the bottom chamber. When liquid flow in the bottom chamber is stopped the pressure equilibrates, causing the membranes to relax back to a resting position and air or gas to exit the top chamber through the port. The liquid flow can be pulsatile (repeated start and stop flow) to simulate breathing. Rather than totally stopping the liquid flow, the flow rate can be reduced to increase the pressure in the bottom chamber relative to the pressure in the bottom chamber that results from a higher flow rate. A first pump state can correspond to the higher flow rate and the second pump state can correspond to a flow rate lower than the higher flow rate. Alternatively, the flow rate can be reversed in the second pump state to more rapidly increase the pressure in the lower chamber. The rate of inhaling air into and exhaling air from the device can be varied by controlling the flow rates and flow direction.

In particular embodiments, a cell culture medium is utilized in the disclosed devices. The fluid includes components that support the viability and function of the plurality of cells one or both sides of the membrane in the device, including components such as inorganic salts and/or minerals, amino acids, energy-providing components, vitamins and/or cofactors, supplements, trace elements, organic acids, salts, and/or esters, antibiotics, and/or protein growth factors. In some examples, the cell culture medium includes those disclosed in International Pat. App. Publ. No. WO 2016/049367, which is incorporated herein by reference in its entirety.

In some embodiments, the disclosed devices are used to study drug (or drug candidate) efficacy and/or toxicity. Thus, in some examples, the devices (independently or integrated in a lung model) are used to study lung disorders, such as asthma, chronic obstructive pulmonary disease, cystic fibrosis, infectious diseases (such as influenza, pneumonia, or tuberculosis), lung cancer, and/or acute respiratory distress syndrome. In other examples, the disclosed devices are used to study the flow dynamics of particles in alveoli or lung. The disclosed devices can utilize the same pathway for air intake (inhalation) and outflow (exhalation), akin to a lung, and thus are more physiologically relevant than current organ-on-a-chip technologies, which utilize one-way airflow.

Particular method embodiments disclosed herein include introducing one or more compounds (such as a drug, toxin, stimulus, and/or infectious agent), into a device embodiment disclosed herein and analyzing a response generated after the compound has been introduced into the device. In some embodiments, the device is activated (for example, by cyclical creation and release of a vacuum) before, during, and/or after introducing the one or more compounds. The device may be used independently or integrated into a lung system or platform, as discussed above.

In some embodiments, analyzing a response includes detecting whether a compound causes a change in the way in which the device, or a component thereof, operates. In some embodiments, a control compound is introduced into the device to provide baseline results to be used as a comparison for other compounds of interest that are introduced into the device. Such control compounds may be any compound known to those of ordinary skill in the art to have a known or understood effect on lung activity (e.g., epinephrine, methoxamine, or the like) or may be an inert compound or composition (e.g., buffer or carrier). For example, in some embodiments, the compound can adversely influence or modify one or more of the cell populations associated with various components of the device (e.g., a membrane material) so that the cell population produces responses (e.g., immune responses, physical leakage of fluids between a membrane layer, changes in gene expression, secretion of molecules, cell death or apoptosis, cellular edema, inhibition of gas exchange, or a combination thereof) that can be detected using a suitable detection technique, such as immunohistochemical staining, trans-epithelial electric resistance (TEER) measurements, visual detection, mass spectrometric detection, chromatographic detection or the like.

In some embodiments, a first compound that has any of the above-mentioned adverse effects on one or more components of the device is introduced and then a second compound, such as a therapeutic compound (or potentially therapeutic compound) capable of ameliorating, inhibiting, or stopping the adverse effects, is introduced. The ability of the second compound to ameliorate or stop the adverse effects is them determined by analyzing a sample extracted from the device and determining whether, for example, leakage has been stopped or reduced or if immune responses from the cell populations have stopped or diminished.

The disclosed devices or lung organ devices including the disclosed devices can be further combined with one or more analytical devices capable of analyzing samples obtained from the device. Such devices can be used to analyze a response generated by the lung organ device. For example, devices like chromatographs (gas or liquid), mass spectrometers, or a combination thereof can be used to analyze fluids that are extracted from the lung organ device to detect or determine the presence of drugs, toxins, or other chemical components present in the fluids. In some embodiments, fluids may be extracted from the device using an automated system. The analytical devices can be integrated with or separate from the device, or a component thereof.

B. Vacuum on a Chip

As discussed above, the disclosed devices utilize a pressure drop produced by flow restriction upstream of a bottom chamber, such as at an inlet to the bottom chamber, to mimic lung function by creating a vacuum in the top chamber ("inhaling") and releasing the vacuum to equilibrate pressure ("exhaling").

Figure 18:
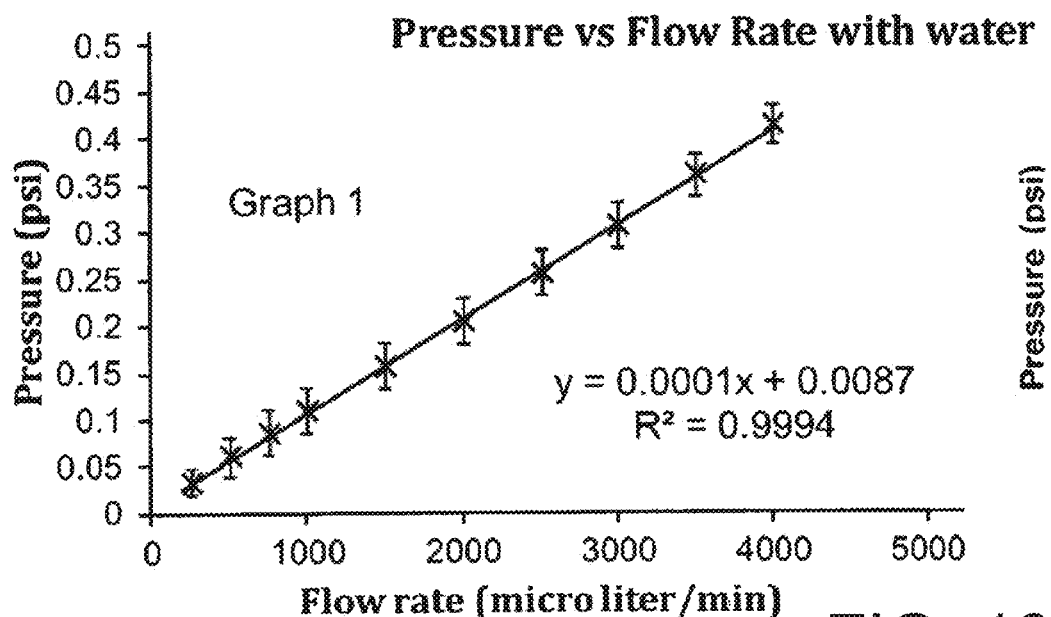
FIG. 18 is a graph showing pressure versus flow rate for water.

However, the disclosed devices can be utilized in any situation where it is desirable to apply a vacuum, essentially acting as a milli- or micro-scale vacuum pump. As illustrated in FIG. 18, in one non-limiting example, the vacuum achieved is proportional to the flow rate in the bottom chamber. A vacuum of up to −68 kPa has been produced in a 27 µl device with N=5 (for example, as illustrated in FIG. 8C at the highest performance. In a vacuum pump application the membrane is typically not provided with pores.

In some embodiments, one end of a connector (such as tubing) is attached to a port 46 communicating with the top chamber and the other end of the connector is attached to a device in which it is desired to create a vacuum. Vacuum is created by flowing liquid through the bottom chamber of the device, creating a pressure drop in the bottom chamber and a vacuum in the upper chamber. The strength of the vacuum can be adjusted, for example by increasing or decreasing the fluid flow rate. The vacuum is released by stopping fluid flow in the lower chamber.

In some examples, the disclosed devices can be used to create suction, decrease pressure in a chamber (such as a chamber in a microfluidic device or system), or other applications. In one example, the disclosed devices can be used to provide vacuum in a miniaturized (for example, portable) mass spectrometer.

C. Measurement of Liquid Flow Rate, Presence of Bubbles in a Liquid, Liquid Viscosity, Liquid Temperature, Liquid pH, and/or Concentration of One or More Ions in a Liquid In some embodiments, the devices are utilized to measure liquid flow rate, presence of bubbles in a liquid, liquid viscosity, liquid temperature, liquid pH, and/or concentration of one or more ions in a liquid.

1. Measuring Liquid Flow

In some embodiments, the disclosed devices or systems are used in methods of determining flow rate of a liquid. In some embodiments, the disclosed devices or systems can also be used to detect presence of bubbles in a liquid, for example, in a liquid flowing through the system. In some examples, the device is incorporated into a system with an infusion pump to provide flow rate information and/or the presence of bubbles in the infusion line.

Liquid flow through the device or system (such as flow rate) can be measured based on the relationship between flow rate and pressure. Because the cross-sectional area of the second port is less than the cross-sectional area of the first port, fluid flow through the liquid chamber of the device causes an increase in pressure (if fluid is infused through the first port) or a decrease in pressure (if fluid is withdrawn through the first port). Therefore, in some embodiments, liquid flow rate is determined by flowing or pumping liquid through the device and measuring the pressure in the device. Flow rate can be determined using a standard curve or reference table for flow rate vs. pressure previously determined for the same liquid using the device.

The disclosed devices have a large dynamic range for measuring liquid flow rate. For example, the devices can measure flow rate of about 1 µL/minute to 2500 µL/minute (such as about 0-50 µL/minute, about 10-75 µL/minute, about 30-100 µL/minute, about 50-100 µL/minute, about 75-200 µL/minute, about 150-300 µL/minute, about 250-400 µL/minute, about 300-600 µL/minute, about 500-1000 µL/minute, about 800-1500 µL/minute, or about 1250-2000 µL/minute, or about 1800-2500 µL/minute).

2. Measuring Liquid Viscosity

In some embodiments, the disclosed devices or systems are used in methods of measuring viscosity of a liquid. The membrane deformation (such as through microfluidic aspiration) in the device is a function of the liquid flow rate in the liquid chamber of the device as well as the viscosity of the liquid in the liquid chamber of the device. Thus, in some examples, liquid viscosity is determined by flowing or pumping liquid through the device at a known flow rate(s) and measuring the pressure in the device.

In one example, for a rectangular channel (such as that shown in FIGS. 15 and 24A-24B), pressure drop inside the channel can be described as follows:

$$\Delta P = \frac{12\mu LQ}{h^3 w}$$

where ΔP is pressure drop in the device caused by flow restriction; μ is the viscosity of the liquid; Q is the flow rate; L is the chamber length; h is the chamber height; and w is the chamber width. Thus, viscosity of liquid in the bottom chamber can be calculated if pressure drop, flow rate, and chamber length, height, and width are known. Likewise, the flow rate of the liquid can be calculated if pressure drop, liquid viscosity, and chamber length, height, and width are known.

In additional examples, liquid viscosity may be determined based on previously generated reference values or standard curves. For example, a standard curve showing the pressure generated in a device with known parameters using a liquid of known viscosity at a range of flow rates can be generated. Based on the standard curve (or set of standard curves), viscosity of a liquid can be determined by flowing liquid through the device at a known rates, measuring the resulting pressure and determining the slope of the resulting curve. This value can then be used to determine fluid viscosity using the standard curves or reference tables or values.

Figure 16:
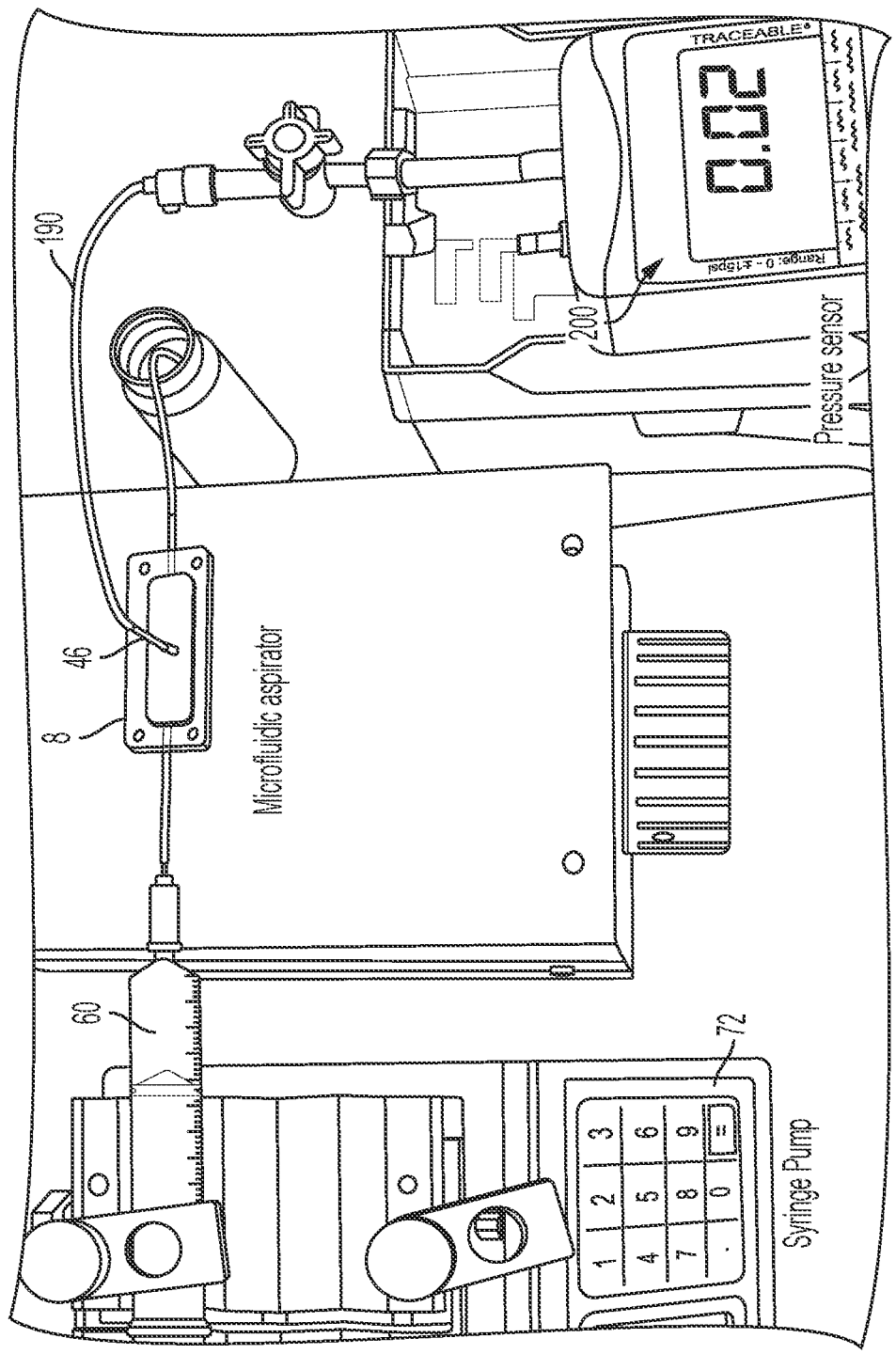
FIG. 16 is a perspective view of an aspirator in accordance with this disclosure having a top chamber port coupled to a pressure sensor for use in, for example, viscosity measurements or flow rate determinations.
Figure 17:
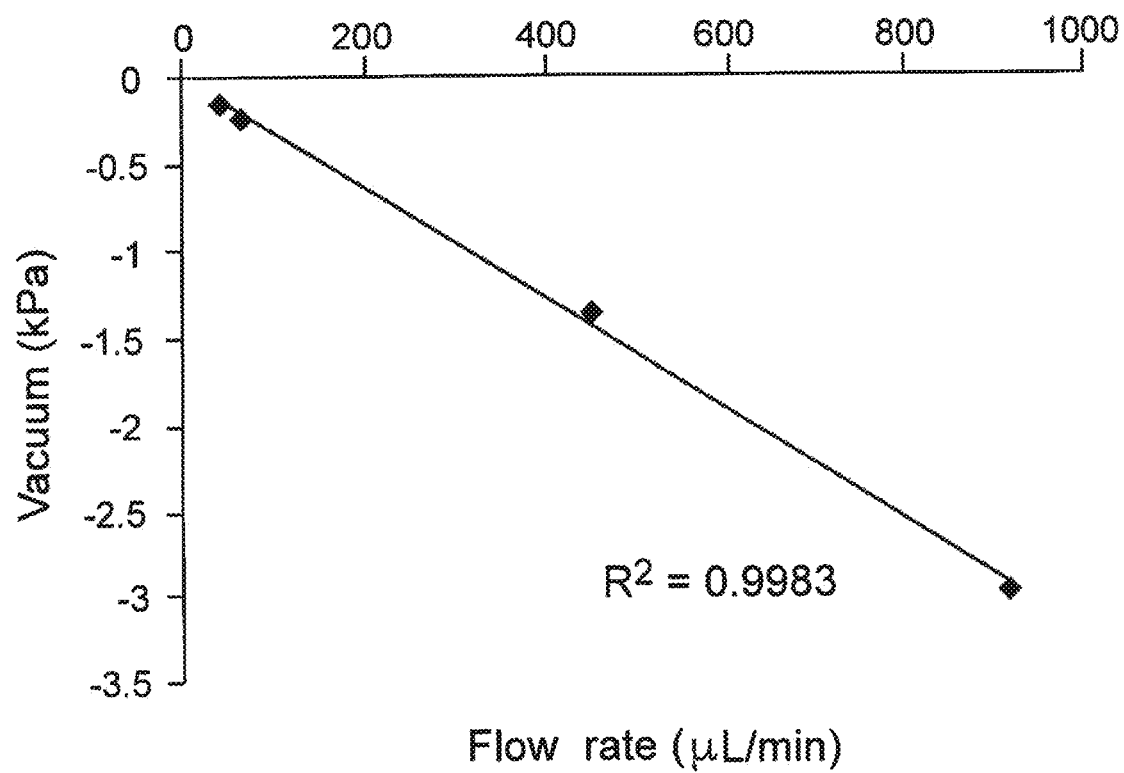
FIG. 17 is a graph showing the effect of flow rate on vacuum in an exemplary embodiment.
Figure 19:
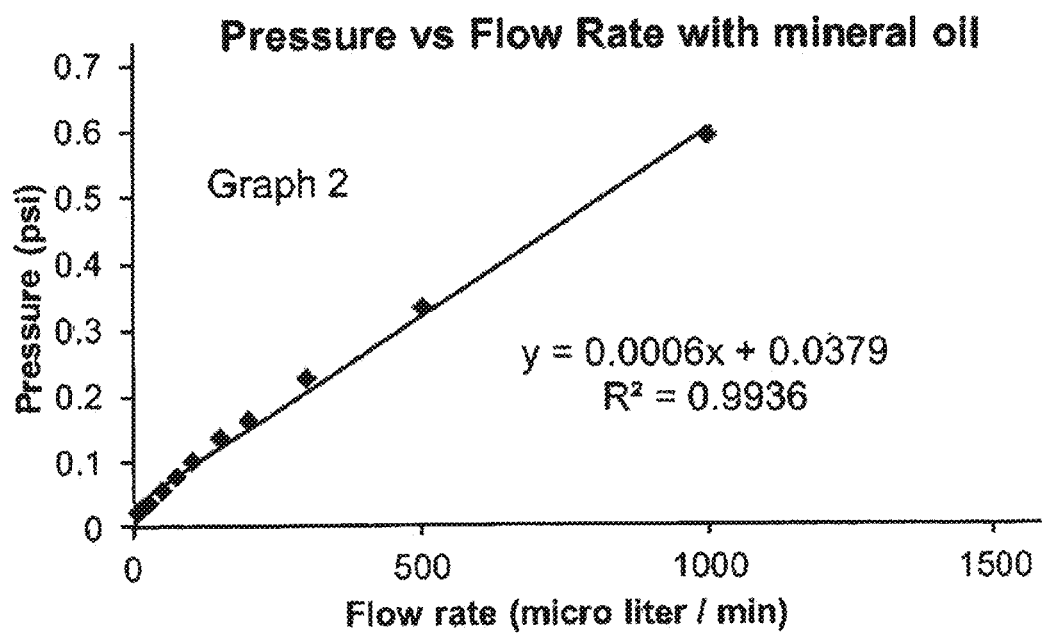
FIG. 19 is a graph showing pressure versus flow rate for mineral oil.

As shown in FIG. 16, a pressure sensor can be connected to the port 46 communicating with the top chamber to measure the pressure drop caused by changes in the liquid flow rate through the lower chamber. Since the chamber dimensions are known, by measuring the pressure drop during liquid flow, the flow rate for a given viscosity liquid can be determined. Alternatively, the viscosity of a liquid for a given flow rate can be determined. FIG. 18 is a graph of pressure versus liquid flow rate for water. FIG. 19 is a graph of pressure versus liquid flow rate for mineral oil. This data is from the operation of a five-well version (the aspirator of FIG. 8C) with a 35 μm PDMS pore free membrane and openings 30 A-E and 82 A-E that were 4 mm. The data shown in FIG. 17 was also obtained from operation of this device.

In other examples, the top chamber 12 of the aspirator device is filled with a liquid (for example, a liquid containing a dye), such that the liquid at least partly extends into the port 46. In some examples, the port may be longer and/or wider than in devices utilized in other uses herein, for example, to better visualize the meniscus formed by the liquid in the top chamber. Displacement of the meniscus of the liquid in the top chamber can be observed during flow of liquid through the bottom chamber. The displacement of the meniscus is proportional to the flow rate of the liquid in the bottom chamber for a given viscosity and is proportional to viscosity of the liquid in the bottom chamber for a given flow rate.

The disclosed devices can be utilized as a flow or viscosity sensor for any fluidic or microfluidic applications. In some examples, the disclosed devices can be included in a microfluidic chip or system (such as those described in International Pat. App. Publ. Nos. WO 2016/049363 and WO 2016/049365) to provide an integrated flow and/or viscosity sensor. In some examples, the flow and/or viscosity sensor element (such as the disclosed device) includes one or more sensors (such as a pressure sensor or optical sensor) that receives input from the device. The device and/or the sensors can be connected to an electronic module (such as a computer) that receives information and provides an output, such as a flow or viscosity reading. In some examples, the electronic module may also be utilized to set operating conditions, such as flow rate or to stop and start flow. These parameters can be manually, semi-automatically, or automatically controlled.

3. Measuring Other Liquid Characteristics

The disclosed devices and systems, including a stimulus-responsive packed bed, can be used to determine other characteristics, including pH, temperature, and ion concentrations. As discussed above, in some embodiments, the device or system includes a packed bed of stimulus responsive material in the second port. The material has a known response to a particular characteristic (such as shrinking or swelling). Therefore, in some embodiments, liquid flow rate is determined by flowing or pumping liquid through the device containing the stimulus-responsive packed bed and measuring the pressure in the device. The characteristic of interest can be determined using a standard curve or reference table or value for the characteristic vs. pressure previously determined for the same liquid using the device.

D. Tunable Lens

With reference to FIG. 20 and FIGS. 21-23, an application of the technology disclosed herein to tuning or adjusting the focal point of a lens is described.

Figure 20:
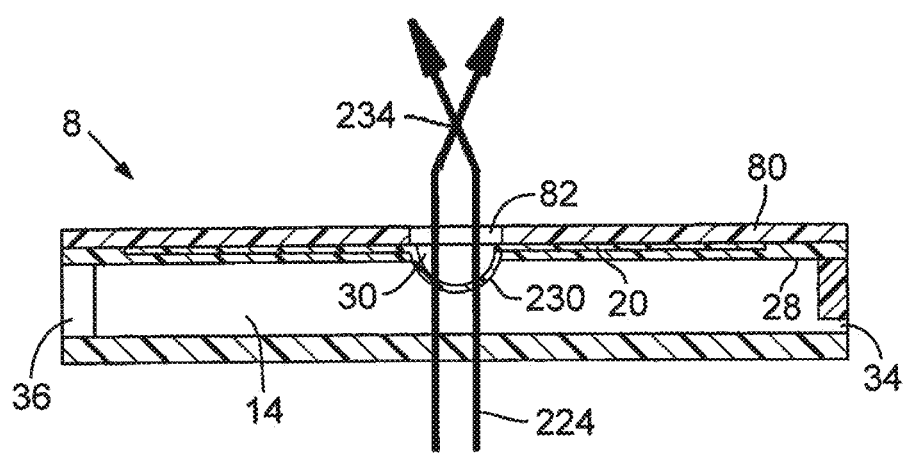
FIG. 20 shows an aspirator in accordance with this disclosure modified for use as a tunable lens.

In FIG. 20, the top chamber 12 is eliminated and a bottom liquid flow chamber 14 with at least one inlet 34 and at least one outlet 36 is disclosed. A flow restriction as previously described is placed at or upstream of the inlet 34 to chamber 14. The bottom wall of the bottom chamber is light transmissive and/or includes a light trans-missive section, such as of glass or polymer material. Light 224 is shown passing upwardly through the bottom wall of the bottom chamber. The membrane 20 comprises a lens, and is positioned as previously described between, in this example, substrates 28 and 80. The light 224 is shown passing upwardly through openings 30 and 82 and through a lens 230 (a portion of membrane 20) between substrates 28, 80 in FIG. 20. With liquid flow stopped, the lens 230 is relaxed to a planar state and is positioned perpendicular to the path of light 224 through the lens 230. In response to liquid flow through the chamber 14 from the inlet 34 to the outlet 36, pressure drops in the chamber 14. As a result, the membrane 20 bulges toward chamber 14 as shown in FIG. 20. The extent of the bulging corresponds to the pressure drop in chamber 14 and to the flow rate of liquid. The lens is shown to have a hypothetical focal point at 234. Desirably the openings 30, 82 are circular so that the lens becomes a convex spherical lens as it bulges inwardly in this example. By changing the extent of bulging, the focal length can be changed.

Figure 21:
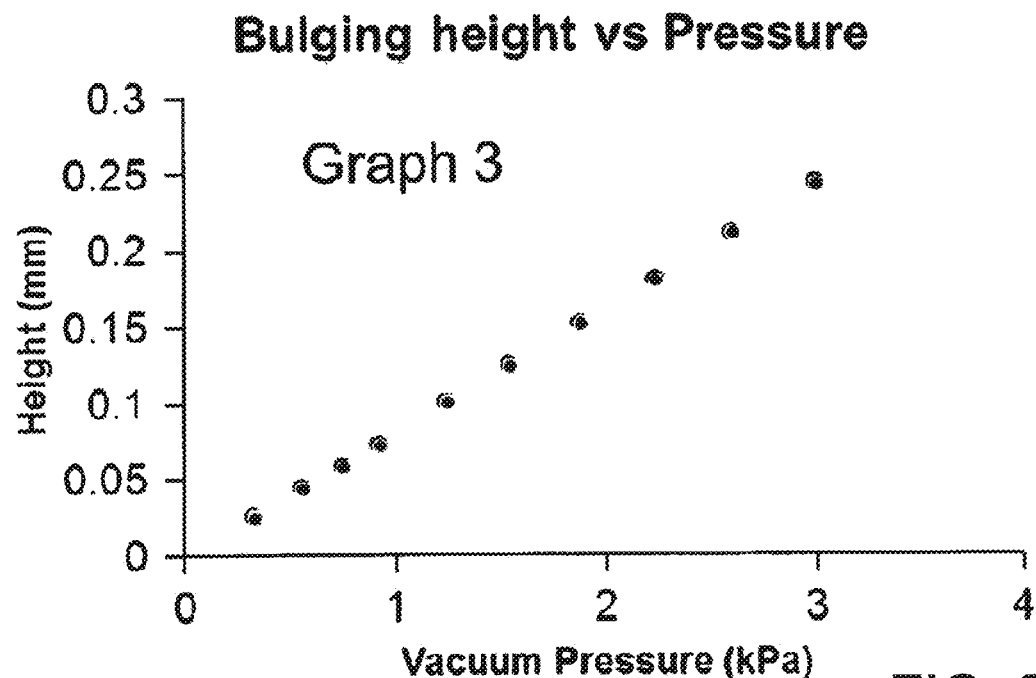
FIG. 21 is a graph showing lens bulging height versus pressure.
Figure 22:
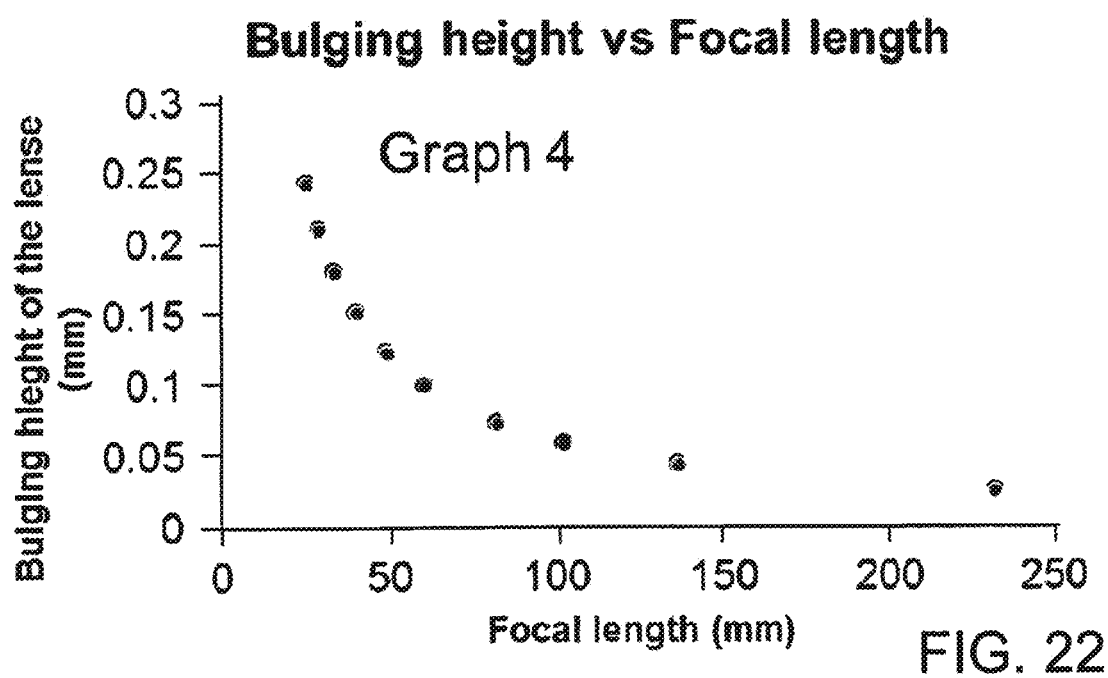
FIG. 22 is a graph showing bulging height versus focal length.
Figure 23:
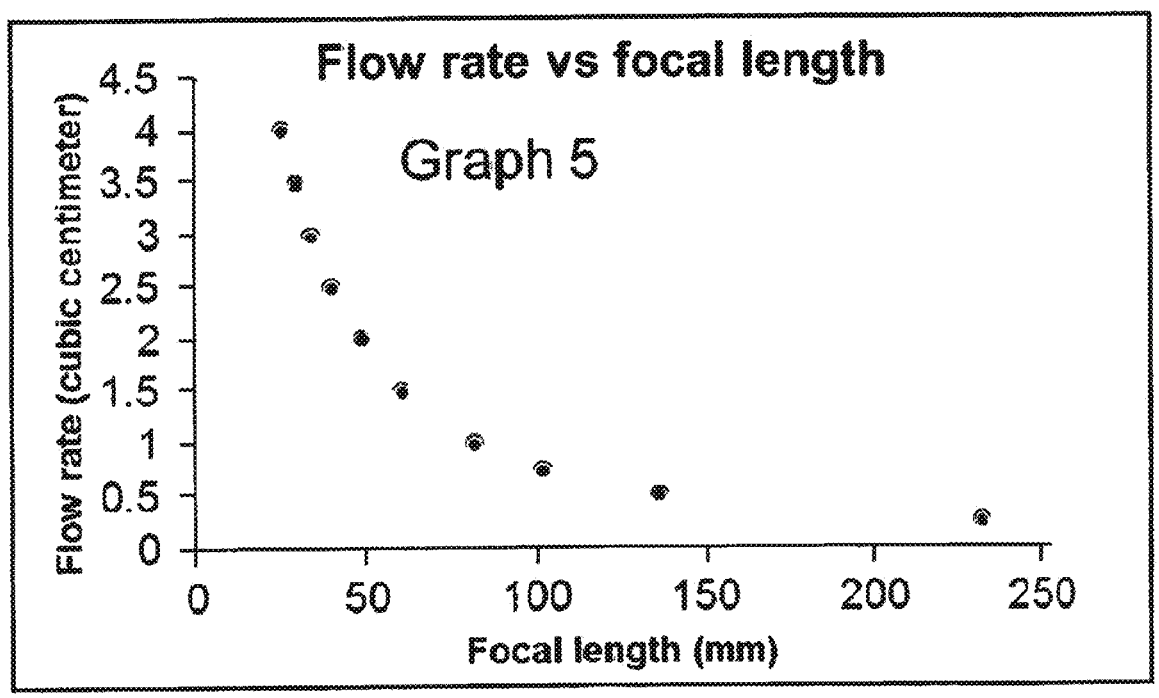
FIG. 23 is a graph showing flow rate versus focal length.

The term bulging height refers to the distance the most distal portion (typically the center of the lens) of the lens has moved from its relaxed position. FIG. 21 illustrates an example of a graph of bulging height versus pressure in chamber 14. By changing the pressure drop (vacuum) in chamber 14, one can vary the bulging height and change the focal length and tune the lens to the desired focal length. FIG. 22 illustrates an example of a graph of focal length versus bulging height for the apparatus of FIG. 20. Finally, FIG. 23 is a graph of flow rate versus focal length for the apparatus of FIG. 20. As one can see, controlling the flow rate, by for example controlling the rate of pumping liquid by a pump coupled to the outlet 36, one can control the focal length and tune the lens 230. The data in FIGS. 21-23 is based on calculations from pressure versus flow rate and experimental data.

EXAMPLES

The following examples are illustrative of disclosed embodiments. In light of this disclosure, those of ordinary skill in the art will recognize that variations of these examples and other examples of the disclosed technology would be possible without undue experimentation.

Example 1

Measuring Liquid Flow Rate

A flow sensor as shown in FIGS. 24A-24B and 25A-25D was constructed. The first port had a diameter of 1.0 mm, and the second port had a diameter of 0.1 mm. The device included a Honeywell® HSCSSNN001PD2A3 pressure sensor coupled to the port in the air chamber. The first port was coupled to a pump by tubing, and the second port was coupled to a liquid reservoir by tubing (silicone tubing with an inner diameter of 1.3 mm). The pressure sensor provided output via a Raspberry Pi device.

Figure 26A:
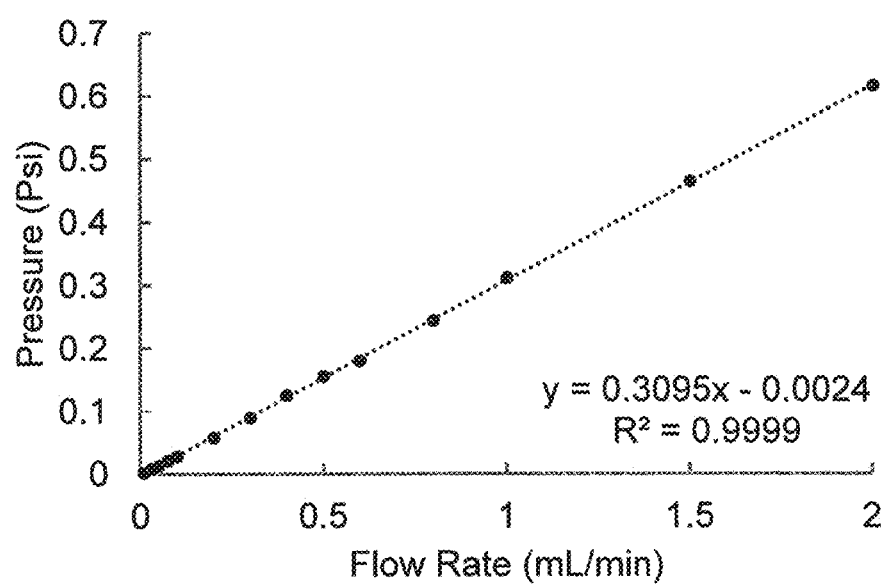
FIGS. 26A and 26B are graphs showing calibration of a flow sensor using a syringe pump with the indicated flow rates.
Figure 26B:
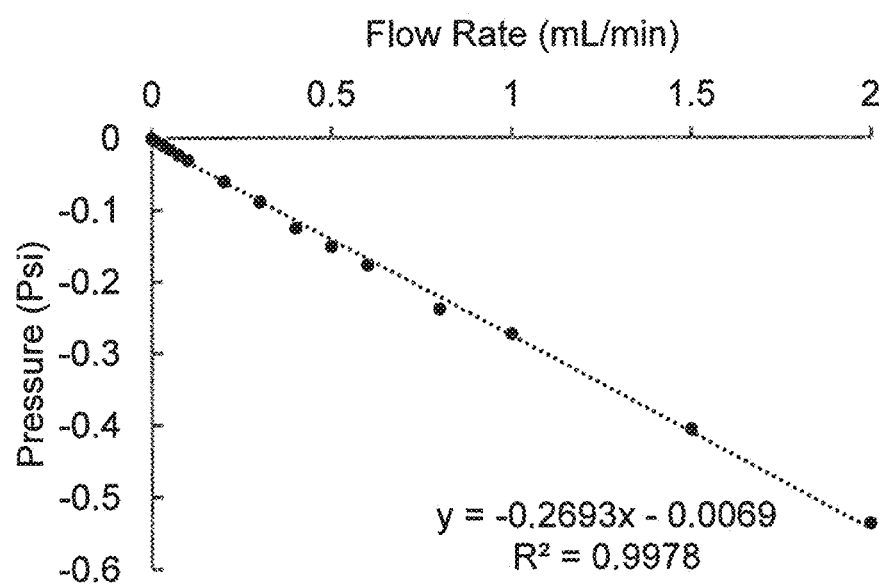

The effect of flow rate on pressure was determined when water was infused through the first port (FIG. 26A) or withdrawn through the first port (FIG. 26B) using a syringe pump. The relationship of flow rate to pressure in both states was linear over the measured flow rates (from 0-2 mL/minute).

Figure 27:
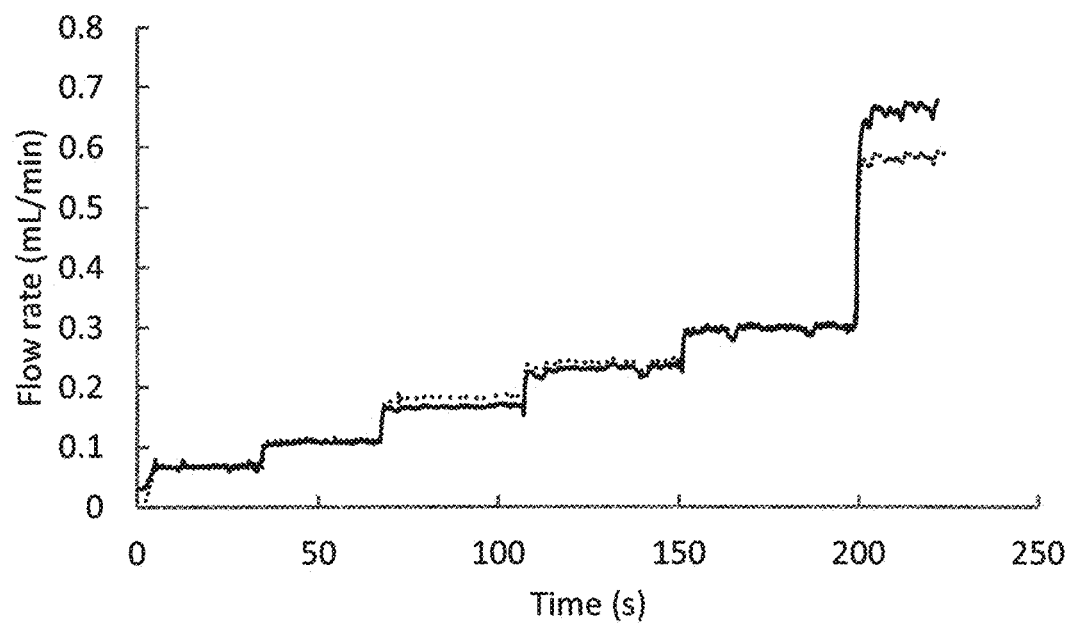
FIG. 27 is a graph showing measurement of infused flow produced by a syringe pump using a commercial flow sensor (dotted line) or a flow sensor of the present disclosure (solid line).
Figure 28:
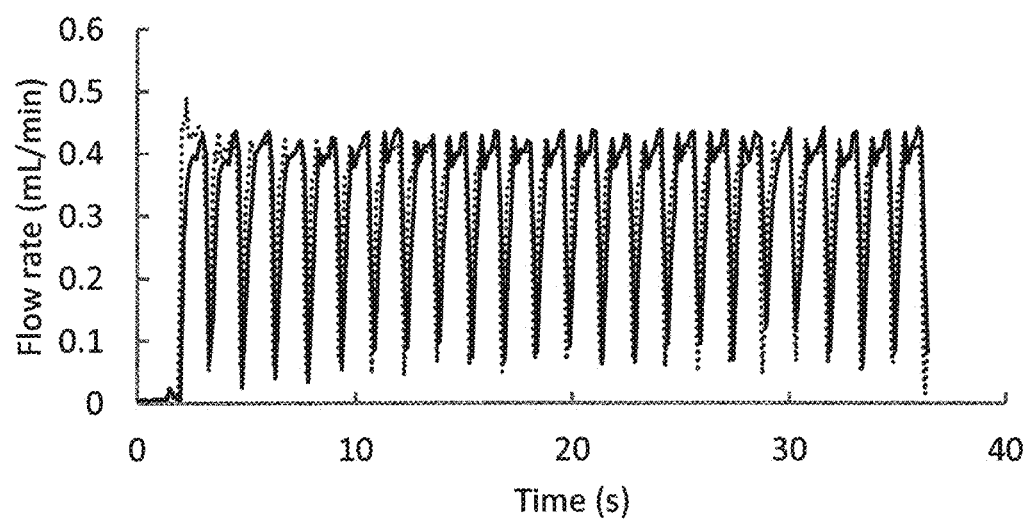
FIG. 28 is a graph showing measurement of pulsatile flow produced by a peristaltic pump using a commercial flow sensor (dotted line) or a flow sensor of the present disclosure (solid line).
Figure 30:
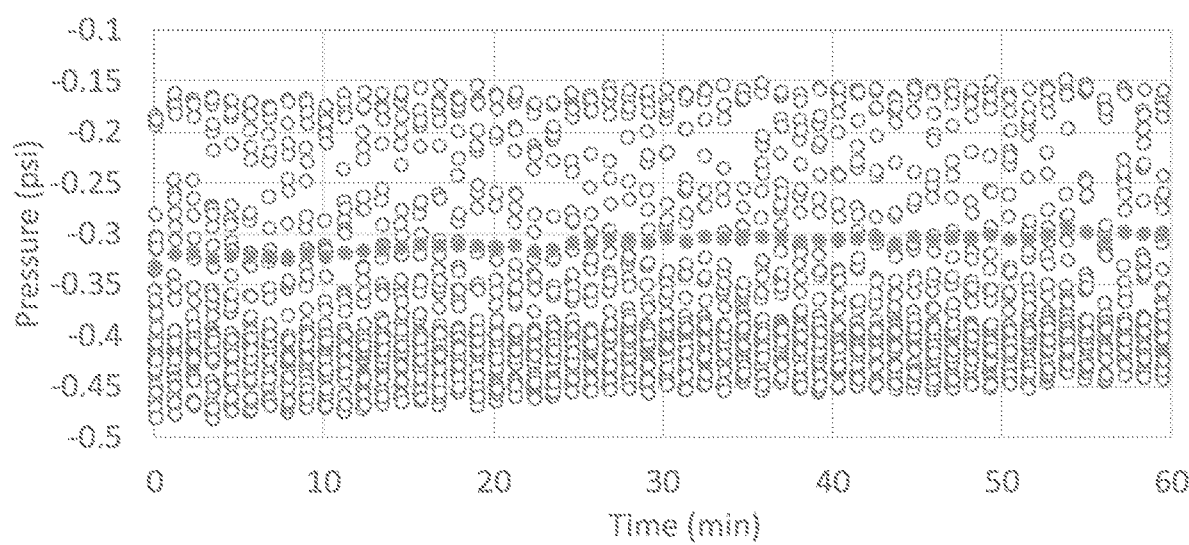
FIG. 30 is a graph showing stability of the sensor connected to a peristaltic pump. Data were recorded every 30 seconds.
Figure 31:
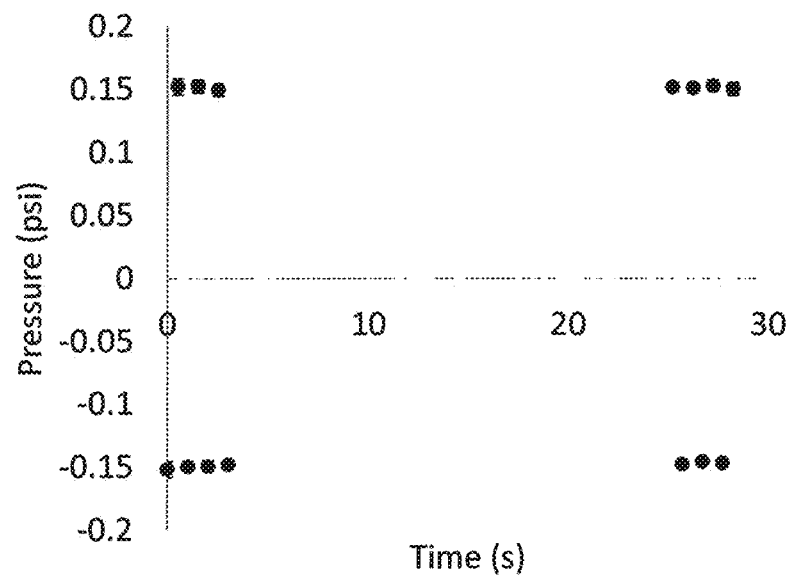
FIG. 31 is a graph showing a fatigue test of the sensor connected to a syringe pump with alternating withdrawal and infusion modes. The data were recorded for 4 minutes at the first and last points within 30 minutes.

The device was compared to a commercial liquid flow sensor (Sensirion Liquid Flow Meter SLI). For the flow sensor device described herein, flow rate was calculated by measuring pressure and then using a previously generated standard curve to determine flow rate. In addition, flow rate was calculated by measuring the weight of water pumped over a given time. As shown in FIG. 27, the performance of the microfluidic device with a syringe pump was generally comparable to that of the commercial sensor at lower flow rates, but diverged at higher flow rates. In addition, performance was stable (FIGS. 28 and 30) and comparable to the commercial sensor (FIG. 28) when a peristaltic pump was used. In another test, the device was used with a syringe pump connected to the first port and set at 500 µL/minute alternating from withdraw to infusion every 30 seconds for 30 minutes. FIG. 31 shows the data recorded for 4 minutes at the first and last points within 30 minutes.

Figure 32:
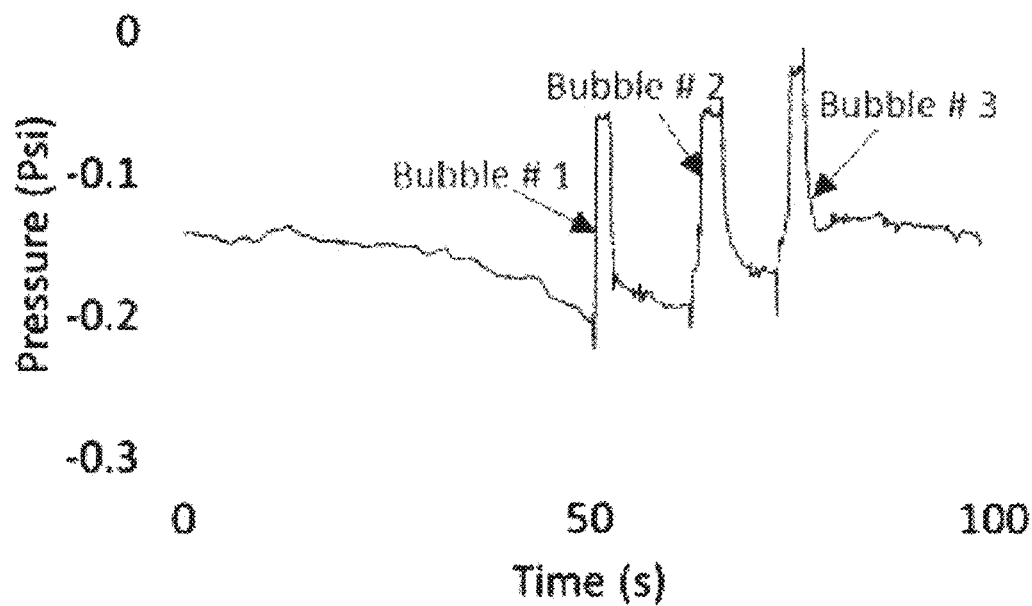
FIG. 32 is a graph showing the effect of the presence of air bubbles in liquid flowing through the sensor on the pressure.

The device is also able to detect presence of bubbles in the sensor. FIG. 32 illustrates the effect of air bubbles in the liquid flowing through the sensor on the pressure reading.

Example 2

Measuring Liquid Viscosity

Figure 33:
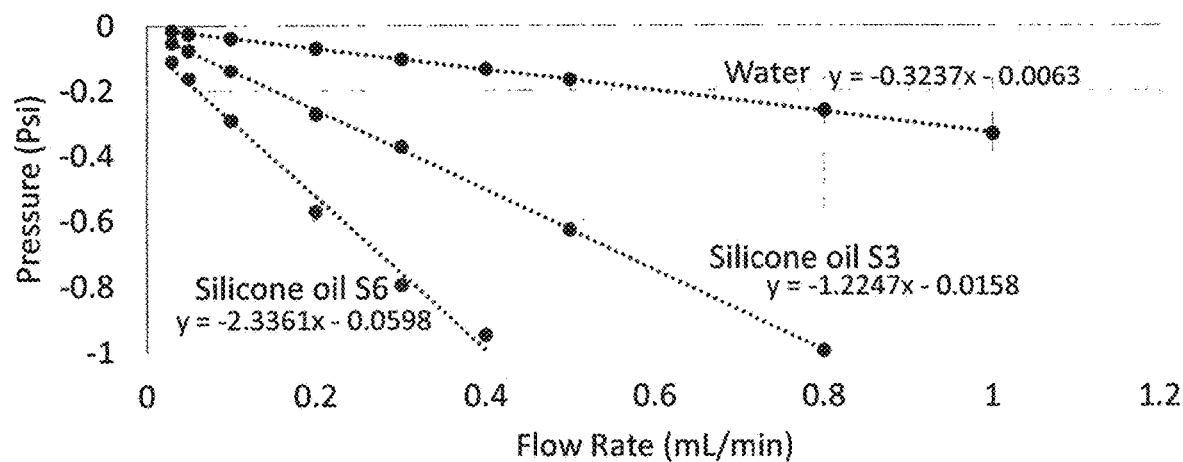
FIG. 33 is a graph showing the relationship of pressure and flow rate with solutions of different viscosity. Water, silicone oil S3, and silicone oil S6 were used.

The device described in Example 1 was used to measure pressure at various flow rates with liquids of differing viscosity. Water, silicone oil S3, and silicone oil S6 were used in the device. The resulting plot of flow rate vs. pressure for each liquid is shown in FIG. 33. The actual and measured viscosity of the liquids is shown in Table 1.

TABLE 1

Measured and actual viscosity measured using microfluidic viscometer

| Liquid | Actual viscosity (cP) | Slope | Measured viscosity (cP) |
|---|---|---|---|
| Water | 0.9795 | −0.3237 | |
| S3 | 3.635 | −1.2247 | 3.706 |
| S6 | 8.480 | −2.3361 | 7.069 |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A device comprising:
    a housing comprising:
        (i) a liquid chamber comprising a first port and a second port, wherein the ratio of the cross-sectional area of the first port to the second port is 10:1;
        (ii) an air chamber comprising a port; and
        (iii) a flexible membrane between the liquid chamber and the air chamber, wherein the membrane comprises a boundary edge and first and second side surfaces, wherein at least a portion of the first side surface is fluidly coupled to the liquid chamber and at least a portion of the second side surface is fluidly coupled to the air chamber, wherein the membrane deflects into the air chamber in response to an increase in pressure in the liquid chamber or deflects into the liquid chamber in response to a decrease in pressure in the liquid chamber; and
    a pressure sensor coupled to the port in the air chamber and having at least one electrical connection that can provide an output.

2. The device of claim 1, further comprising liquid in the liquid chamber.

3. The device of claim 1, wherein the membrane comprises a flexible polymer.

4. The device of claim 1, further comprising a pump fluidly coupled to the first port of the liquid chamber and/or a reservoir fluidly coupled to the second port.

5. The device of claim 1, further comprising an electronic module coupled to the electrical connection of the pressure sensor.

6. A system comprising:
    the device of claim 1;
    a liquid reservoir fluidly coupled to the second port of the device;
    a pump fluidly coupled to the first port of the device; and
    an electronic module coupled to the electrical connection of the pressure sensor.

7. The system of claim 6, wherein the pump is a syringe pump, a peristaltic pump, a pneumatic pump, a piston pump, or an infusion pump.

8. The system of claim 6, further comprising liquid in the liquid chamber.

9. The system of claim 6, wherein the pump operates to pump liquid into the first port in the liquid chamber and increases the pressure in the liquid chamber so that the membrane moves toward the air chamber.

10. The system of claim 6, wherein the pump operates to pump liquid out of the first port in the liquid chamber and decreases the pressure in the liquid chamber so that the membrane moves toward the liquid chamber.

11. A method of determining liquid flow rate, comprising:
    pumping liquid into the first port of the liquid chamber or pumping liquid out of the first port of the liquid chamber of the system of claim 6;
    measuring the pressure in the air chamber produced by pumping the liquid; and
    determining the liquid flow rate.

12. The method of claim 11, wherein the liquid flow rate is determined using a reference value or standard curve.

13. A method of determining liquid viscosity, comprising:
pumping liquid into the first port of the liquid chamber or pumping liquid out of the first port of the liquid chamber of the system of claim 6;
measuring the pressure in the air chamber produced by pumping the liquid; and
determining the viscosity of the liquid.

14. The method of claim 13, wherein the liquid viscosity is determined using a reference value or standard curve.

15. A device comprising:
a housing comprising:
   a liquid chamber comprising a first port and a second port, wherein the cross-sectional area of the first port and the second port are substantially the same;
   tubing connected to the second port, wherein the ratio of the cross-sectional area of the second port to at least a portion of a section of the tubing is 10:1;
   an air chamber comprising a port; and
   a flexible membrane between the liquid chamber and the air chamber, wherein the membrane comprises a boundary edge and first and second side surfaces, wherein at least a portion of the first side surface is fluidly coupled to the liquid chamber and at least a portion of the second side surface is fluidly coupled to the air chamber, wherein the membrane deflects into the air chamber in response to an increase in pressure in the liquid chamber or deflects into the liquid chamber in response to a decrease in pressure in the liquid chamber; and
a pressure sensor coupled to the port in the air chamber and having at least one electrical connection that can provide an output.

* * * * *